(12) United States Patent
Altier et al.

(10) Patent No.: US 7,589,176 B2
(45) Date of Patent: Sep. 15, 2009

(54) ANTIFUNGAL POLYPEPTIDES

(75) Inventors: Daniel J. Altier, Waukee, IA (US); Irina Ellanskaya, Kyiv (UA); Natalia Ellanskaya, legal representative, Kyiv (UA); Jacob T. Gilliam, Norwalk, IA (US); Jennie Hunter-Cevera, Elliott City, MD (US); James K. Presnail, Avondale, PA (US); Eric Schepers, Port Deposit, MD (US); Carl R. Simmons, Des Moines, IA (US); Tamas Torok, Richmond, CA (US); Nasser Yalpani, Johnston, IA (US)

(73) Assignees: Pioneer Hi-Bred International, Inc., Johnston, IA (US); E. I. du Pont de Nemours and Company, Wilmington, DE (US); The Regents of the University of California, Oakland, CA (US)

( * ) Notice: Subject to any disclaimer, the term of this patent is extended or adjusted under 35 U.S.C. 154(b) by 132 days.

(21) Appl. No.: 11/657,710

(22) Filed: Jan. 24, 2007

(65) Prior Publication Data

US 2007/0192899 A1 Aug. 16, 2007

Related U.S. Application Data

(60) Provisional application No. 60/762,065, filed on Jan. 25, 2006.

(51) Int. Cl.
*C07K 14/00* (2006.01)
*C07K 14/415* (2006.01)
*C07K 17/00* (2006.01)
(52) U.S. Cl. .................. 530/370; 530/350; 530/324; 424/404

(58) Field of Classification Search .................. None
See application file for complete search history.

(56) References Cited

U.S. PATENT DOCUMENTS

| 6,573,361 B1 | 6/2003 | Bunkers et al. |
| 2004/0214272 A1 | 10/2004 | La Rosa et al. |

FOREIGN PATENT DOCUMENTS

| WO | WO 98/27805 | 7/1998 |
| WO | WO 2004/048421 A2 | 6/2004 |
| WO | WO 2006/014316 A1 | 2/2006 |

OTHER PUBLICATIONS

The USPTO Publication Site for Issued and Published Sequences (PSIPS), XP002442732, SEQ ID No. 346842 for US 20040214272.
Database EMBL, Jan. 2, 2004, EBI Accession No. EMBL:CF453104, "wt$_{13}$ 2_018 fusarium verticillioides wild type subtraction library *Gibberella moniliformis* cDNA, mRNA sequence", XP002442733.
Database EMBL, Jul. 12, 2001, EBI Accession No. EMBL:BI200659, "o1a11fs.r1 Fusarium sporotrichioides Tri 10 overexpressed cDNA library fusarium sporotrichioides cDNA clone 01a11§ 5' mRNA sequence", XP002442734.
Database EMBL, Jun. 2, 2004, EBI Accession No. EMBL: CN811083, Fg03_12c23_R, Fg03)AAFC_ECORC_Fusarium_ graminearum_mycelium_trichothecene_prodcutr ion *Gibberella zeae* cDNA clone Fg03_12c23, mRNA sequence, XP002442735.
Rey, M, et al., "Unexpected Homology Between Inducible Cell Wall Protein QID74 of Filamentous Fungi and BR3 Salivary Protein of the Insect *Chironomus,* " *Proc. Natl. Acad. Sci. USA*, 1998, pp. 6212-6216, vol. 95.

*Primary Examiner*—Medina A Ibrahim
(74) *Attorney, Agent, or Firm*—Alston & Bird LLP

(57) ABSTRACT

The invention relates to antifungal compositions and methods for protecting a plant from a fungal pathogen. Compositions including antifungal polypeptides isolated from a fungal fermentation broth are provided.

3 Claims, 9 Drawing Sheets

FIG. 1

```
                                    1                                                                   82
LB12265P3A_B_C (SEQ ID NO:1)   (1)  S----ILHHCGKHASWDHAKSECVCHDSGKVYTKKHHKCKCPK------------------GEKWHHIEKKCKK
crln.pk0189.g4 (SEQ ID NO:3)   (1)  S----ILHHCGKHASWDHAKSECVCHDSGKVYTKKHHKCKCPK------------------GEKWHHIEKKCKK
Fve_AFPlike    (SEQ ID NO:5)   (1)  S----ILHHCGKHASWDHAKSECVCHDSGKVYTKKHHKCKCPK------------------GEKWHHIEKKCKK
Fsp_AFPlike    (SEQ ID NO:7)   (1)  SKHH-DHHDCGKHASYNEEKKECVCHASGETYHKKKHKCKKEK-----------------EDKKHKTERDIIA
Gze_AFPlike    (SEQ ID NO:9)   (1)  S--K-HHHDCGKHASYNTEKKECVCHVSGETYHKKHHKCKKPK-----------------EDKKHHSR-DVLE
Hli_AFPlike    (SEQ ID NO:11)  (1)  LVARGGSHDCGSYASWNNGKNCCVCKDNGKNYDSKSKSCNCPSGYTWNGHQCVHDCGKDATWQYGNCVCNKKGEVYNPKDKT
```

FIG. 2-1

```
                                      1                                                                              80
LB12265       (SEQ ID NO:14)      (1) MLLNKAF LGALLAMGT VTALPNP----    -DAEPADLEERS----    -ILHHCGKHASWD HAKSECVCHD SGKVYTKKH HKCKCPK
crln.pk0189.g4 (SEQ ID NO:24)     (1) MLLNKAF LGALLAMGT VTALPNP----    -DAEPVDLED RS---    -ILHHCGKHASWD HAKSECVCHD SGKVYTKKH HCKCPK
Fve_AFPlike   (SEQ ID NO:5)       (1) MLLNKAF LGALLAMGT VTALPNP----    -DAEPVDLED RS---    -ILHHCGKHASWD HAKSECVCHD SGKVYTKKH HCKCPK
Fsp_AFPlike   (SEQ ID NO:7)       (1) MLFNKLF LGAILAMTSV AAIPNP----    -VAEPGSLVE RSKHH-    DHHDCGKHASYN EEKKECVCHA SGETYHKKH KCCKKEK
Gze_AFPlike   (SEQ ID NO:9)       (1) MRFSNLF LGAVFAVTS VAAMANP---    -AAEAGSLME RS---K-    HHHDCGKHASYN TEKKECVCHV SGETYHKKH HCCKPKK
Hli_AFPlike   (SEQ ID NO:11)      (1) MLLKQVL VAALLSLSS VTAFPNPNNL HDVEARDVED NLVARGGSH DCGSYASWNN GKNCCVCKD NGKNYDSKSK SCNCPS 81                                                                             160
LB12265       (SEQ ID NO:14)     (73) ----------- ---------- ---------- ---------- ---------- ---------- -----------
crln.pk0189.g4 (SEQ ID NO:24)    (73) ----------- ---------- ---------- ---------- ---------- ---------- -----------
Fve_AFPlike   (SEQ ID NO:5)      (73) ----------- ---------- ---------- ---------- ---------- ---------- -----------
Fsp_AFPlike   (SEQ ID NO:7)      (76) ---------- ----------- GEKWHHIEK KCKK---- ---------- ---------- -----------
Gze_AFPlike   (SEQ ID NO:9)      (74) ---------- ----------- GEKWHHIEK KCKK---- ---------- ---------- -----------
Hli_AFPlike   (SEQ ID NO:11)     (81) GYTWNGH QCVHDCGKD ATWQYGNCVC NKKKGEVYNP KDKTCSCPPG QYWNGKNCQ VDCGKDASYD YKQKKCVCK KHGEIYN 161                                                                             240
LB12265       (SEQ ID NO:14)     (86) ---------- ---------- ---------- ---------- ---------- ---------- -----------
crln.pk0189.g4 (SEQ ID NO:24)    (86) ---------- ---------- ---------- ---------- ---------- ---------- -----------
Fve_AFPlike   (SEQ ID NO:5)      (86) ---------- ---------- ---------- ---------- ---------- ---------- -----------
Fsp_AFPlike   (SEQ ID NO:7)     (125) KHHKKKCK KS------ KDV KKVVDDKKK AKDDKKSNDK KSDDDKKSK DGKGPKSERD VIAERSPK- ---------KHKDHD
Gze_AFPlike   (SEQ ID NO:9)     (121) KHHKKKCK K------- ------AKDEK KKDDKK---- ---------- ---------HHSR DVLEERDPK- ---------KDKHHD
Hli_AFPlike   (SEQ ID NO:11)    (161) SNSKTCS CPPGQVWNG YACVDCGKE AHFDNKQKK CVCNNYGEIY NSGSKTCAC PGGQYFNGKK CVCPYGKV NGKQCVE 241                                                                             320
LB12265       (SEQ ID NO:14)     (86) ---------- ---------- ---------- ---------- ---------- ---------- -----------
crln.pk0189.g4 (SEQ ID NO:24)    (86) ---------- ---------- ---------- ---------- ---------- ---------- -----------
Fve_AFPlike   (SEQ ID NO:5)      (86) ---------- ---------- ---------- ---------- ---------- ---------- -----------
Fsp_AFPlike   (SEQ ID NO:7)     (189) RCGKHAS YSEEKKECV CHNKAEIFER KHKCKCKHI SLRS---- ---------- -ILHHCGREA YYDDAKNE CICHDSG
Gze_AFPlike   (SEQ ID NO:9)     (159) HCGKHAS YSEEKKECV CHNKAEVFER KHKKCKKHI SLRS---- ---------- -IFNHCGRHA AYYDEAKKE CICHDAG
Hli_AFPlike   (SEQ ID NO:11)    (241) DCGKEAH FDYNQKKCV CKNNGEVYNS AKKTCSCPDG QYWNGKQCV CPYGGKDAT YDYNQKKCV CKNKGEVFDQ KTKTCSCPD GQYWNGK 321                                                                             400
LB12265       (SEQ ID NO:14)     (86) ---------- ---------- ---------- ---------- ---------- ---------- -----------
crln.pk0189.g4 (SEQ ID NO:24)    (86) ---------- ---------- ---------- ---------- ---------- ---------- -----------
Fve_AFPlike   (SEQ ID NO:5)      (86) ---------- ---------- ---------- ---------- ---------- ---------- -----------
Fsp_AFPlike   (SEQ ID NO:7)     (252) KDFLKKH KTCACPQGE KWHHIERKCS RH- ---------- ---------- ---------- -----------
Gze_AFPlike   (SEQ ID NO:9)     (222) KDFLKKH KTCACPQGE KWHHIERKCK A-- ---------- ---------- ---------- -----------
Hli_AFPlike   (SEQ ID NO:11)    (321) EIYDSKT KTCSCPDGQ VWNGKQCVCP YGQVFNGKQ CVPDCGKDAT YDYNQKKCV CKNKGEVFDQ KTKTCSCPD GQYWNGK 401                                                                             480
LB12265       (SEQ ID NO:14)     (86) ---------- ---------- ---------- ---------- ---------- ---------- -----------
crln.pk0189.g4 (SEQ ID NO:24)    (86) ---------- ---------- ---------- ---------- ---------- ---------- -----------
Fve_AFPlike   (SEQ ID NO:5)      (86) ---------- ---------- ---------- ---------- ---------- ---------- -----------
Fsp_AFPlike   (SEQ ID NO:7)     (279) ---------- ---------- ---------- ---------- ---------- ---------- -----------
Gze_AFPlike   (SEQ ID NO:9)     (248) ---------- ---------- ---------- ---------- ---------- ---------- -----------
Hli_AFPlike   (SEQ ID NO:11)    (401) QCACPYG QIFNGKQCV PDCGKDATYD YNQKKCVC NKGEVFDQKT KTCSCPDGQ YWNGKQCVCP YGKIFDGKQ CVEDCGK
```

FIG. 2-2

```
                                    481                                                                     560
LB12265       (SEQ ID NO:14)   (86) ----------------------------------------------------------------------------
crln.pk0189.g4 (SEQ ID NO:24)  (86) ----------------------------------------------------------------------------
Fve_AFPlike   (SEQ ID NO:5)    (86) ----------------------------------------------------------------------------
Fsp_AFPlike   (SEQ ID NO:7)   (279) ----------------------------------------------------------------------------
Gze_AFPlike   (SEQ ID NO:9)   (248) ----------------------------------------------------------------------------
Hli_AFPlike   (SEQ ID NO:11)  (481) DAHFDNNQKKCVCNKNGEIYDSKSKTCSCPDSQYWDGSKCACPYGTVWDGKHCNQDCGKDAHFDSNQKKCVCNKQGEVYD 561                                                                     640
LB12265       (SEQ ID NO:14)   (86) ----------------------------------------------------------------------------
crln.pk0189.g4 (SEQ ID NO:24)  (86) ----------------------------------------------------------------------------
Fve_AFPlike   (SEQ ID NO:5)    (86) ----------------------------------------------------------------------------
Fsp_AFPlike   (SEQ ID NO:7)   (279) ----------------------------------------------------------------------------
Gze_AFPlike   (SEQ ID NO:9)   (248) ----------------------------------------------------------------------------
Hli_AFPlike   (SEQ ID NO:11)  (561) SKSKTCSCPDGQYWDGSKCACPYGKVWDGKQCVPNCGKDASYDSKQNKCVCKNIGQVFDTKSLTCSCPAGTSWNGHACVQ 641                                          704
LB12265       (SEQ ID NO:14)   (86) --------------------------------------------
crln.pk0189.g4 (SEQ ID NO:24)  (86) --------------------------------------------
Fve_AFPlike   (SEQ ID NO:5)    (86) --------------------------------------------
Fsp_AFPlike   (SEQ ID NO:7)   (279) --------------------------------------------
Gze_AFPlike   (SEQ ID NO:9)   (248) --------------------------------------------
Hli_AFPlike   (SEQ ID NO:11)  (641) DCGKDAHYDSNQKCCVCNNKGESYDSKSKTCSCPGNQYWDGNKCACPYGSTWDSSKKTCKMNYP
```

A

ANTIFUNGAL POLYPEPTIDES

CROSS REFERENCE TO RELATED APPLICATIONS

This application claims the benefit of U.S. Provisional Application No. 60/762,065, filed on Jan. 25, 2006, which is herein incorporated by reference in its entirety.

FEDERALLY SPONSORED RESEARCH OR DEVELOPMENT

This invention was made with government support under contract number DE-AC02-05CH11231 awarded by the United States Department of Energy. The government has certain rights in the invention.

FIELD OF THE INVENTION

The present invention relates to polypeptides having antipathogenic activity and the nucleic acid sequences that encode them. Methods of the invention utilize these antipathogenic polypeptides and nucleic acid sequences to control plant pathogens and to increase pathogen resistance in plants.

BACKGROUND OF THE INVENTION

Plant diseases are often a serious limitation on agricultural productivity and therefore have influenced the history and development of agricultural practices. A variety of pathogens are responsible for plant diseases, including fungi, bacteria, viruses, and nematodes. Among the causal agents of infectious diseases of crop plants, however, fungi are the most economically important group of plant pathogens and are responsible for huge annual losses of marketable food, fiber, and feed.

Incidence of plant diseases has traditionally been controlled by agronomic practices that include crop rotation, the use of agrochemicals, and conventional breeding techniques. The use of chemicals to control plant pathogens, however, increases costs to farmers and causes harmful effects on the ecosystem. Consumers and government regulators alike are becoming increasingly concerned with the environmental hazards associated with the production and use of synthetic agrochemicals for protecting plants from pathogens. Because of such concerns, regulators have banned or limited the use of some of the most hazardous chemicals. The incidence of fungal diseases has been controlled to some extent by breeding resistant crops. Traditional breeding methods, however, are time-consuming and require continuous effort to maintain disease resistance as pathogens evolve. See, for example, Grover and Gowthaman (2003) *Curr. Sci.* 84:330-340. Thus, there is a significant need for novel alternatives for the control of plant pathogens that possess a lower risk of pollution and environmental hazards than is characteristic of traditional agrochemical-based methods and that are less cumbersome than conventional breeding techniques.

Many plant diseases, including, but not limited to, maize stalk rot and ear mold, can be caused by a variety of pathogens. Stalk rot, for example, is one of the most destructive and widespread diseases of maize. The disease is caused by a complex of fungi and bacteria that attack and degrade stalks near plant maturity. Significant yield loss can occur as a result of lodging of weakened stalks as well as premature plant death. Maize stalk rot is typically caused by more than one fungal species, but *Gibberella* stalk rot, caused by *Gibberella zeae*, *Fusarium* stalk rot, caused by *Fusarium verticillioides*, *F. proliferatum*, or *F. subglutinans*, and Anthracnose stalk rot, caused by *Colletotrichum graminicola* are the most frequently reported (Smith and White (1988); Diseases of corn, pp. 701-766 in Corn and Corn Improvement, Agronomy Series #18 (3rd ed.), Sprague, C. F., and Dudley, J. W., eds. Madison, Wis.). Due to the fact that plant diseases can be caused by a complex of pathogens, broad spectrum resistance is required to effectively mediate disease control. Thus, a significant need exists for antifungal compositions that target multiple stalk rot and ear mold-causing pathogens.

Recently, agricultural scientists have developed crop plants with enhanced pathogen resistance by genetically engineering plants to express antipathogenic proteins. For example, potatoes and tobacco plants genetically engineered to produce an antifungal endochitinase protein were shown to exhibit increased resistance to foliar and soil-borne fungal pathogens. See Lorito et al. (1998) *Proc. Natl. Acad. Sci.* 95:7860-7865. Moreover, transgenic barley that is resistant to the stem rust fungus has also been developed. See Horvath et al. (2003) *Proc. Natl. Acad. Sci.* 100:364-369. A continuing effort to identify antipathogenic agents and to genetically engineer disease-resistant plants is underway.

Thus, in light of the significant impact of plant pathogens, particularly fungal pathogens, on the yield and quality of crops, new compositions and methods for protecting plants from pathogens are needed. Methods and compositions for controlling multiple fungal pathogens are of particular interest.

BRIEF SUMMARY OF THE INVENTION

Compositions and methods for protecting a plant from a pathogen are provided. The compositions include nucleotide and amino acid sequences for antipathogenic, particularly antifungal, polypeptides. The polypeptides of the invention display antipathogenic activity against plant fungal pathogens. More particularly, the compositions of the invention comprise the antipathogenic polypeptide set forth in SEQ ID NO:1, and variants and fragments thereof. Nucleic acid molecules comprising nucleotide sequences that encode the antipathogenic polypeptides of the invention are further provided. Domains of antipathogenic polypeptides, and the nucleotide sequences that encode them, that possess antipathogenic, more particularly antifungal activity are further provided. The domains also find use in screening candidate polypeptides for antipathogenic activity. Thus, the antipathogenic polypeptides of the invention include the domains set forth in SEQ ID NOs:9, 35, 36, and 37 and polypeptides comprising at least one domain sequence selected from this group. Compositions also include expression cassettes comprising a promoter operably linked to a nucleotide sequence that encodes an antipathogenic polypeptide of the invention or domain thereof. Transformed plants, plant cells, seeds, and microorganisms comprising an expression cassette of the invention are further provided.

The compositions of the invention are useful in methods directed to inducing pathogen resistance, particularly fungal resistance, in plants. In particular embodiments, the methods comprise introducing into a plant at least one expression cassette comprising a promoter operably linked to a nucleotide sequence that encodes an antipathogenic polypeptide of the invention. As a result, the antipathogenic polypeptide or antipathogenic polypeptide domain is expressed in the plant, and the pathogen is exposed to the protein at the site of pathogen attack, thereby leading to increased pathogen resistance. A tissue-preferred promoter may be used to drive expression of an antipathogenic protein in specific plant tissues that are particularly vulnerable to pathogen attack, such as, for example, the roots, leaves, stalks, vascular tissues, and seeds. Pathogen-inducible promoters may also be used to drive expression of an antipathogenic protein of the invention, or domain thereof, at or near the site of pathogen infection.

The present invention further provides antipathogenic compositions and formulations and methods for their use in protecting a plant from a pathogen, particularly a fungal pathogen. In some embodiments, compositions comprise an antipathogenic polypeptide (or domain thereof) or a transformed microorganism comprising a nucleotide sequence encoding an antipathogenic polypeptide of the invention (or domain thereof) in combination with a carrier. Methods of using these compositions to protect a plant from a pathogen comprise applying the antipathogenic composition to the environment of the plant pathogen by, for example, spraying, dusting, broadcasting, or seed coating. The methods and compositions of the invention find use in protecting plants from pathogens, including fungal pathogens, viruses, nematodes, and the like.

DETAILED DESCRIPTION OF THE INVENTION

Figure 3:
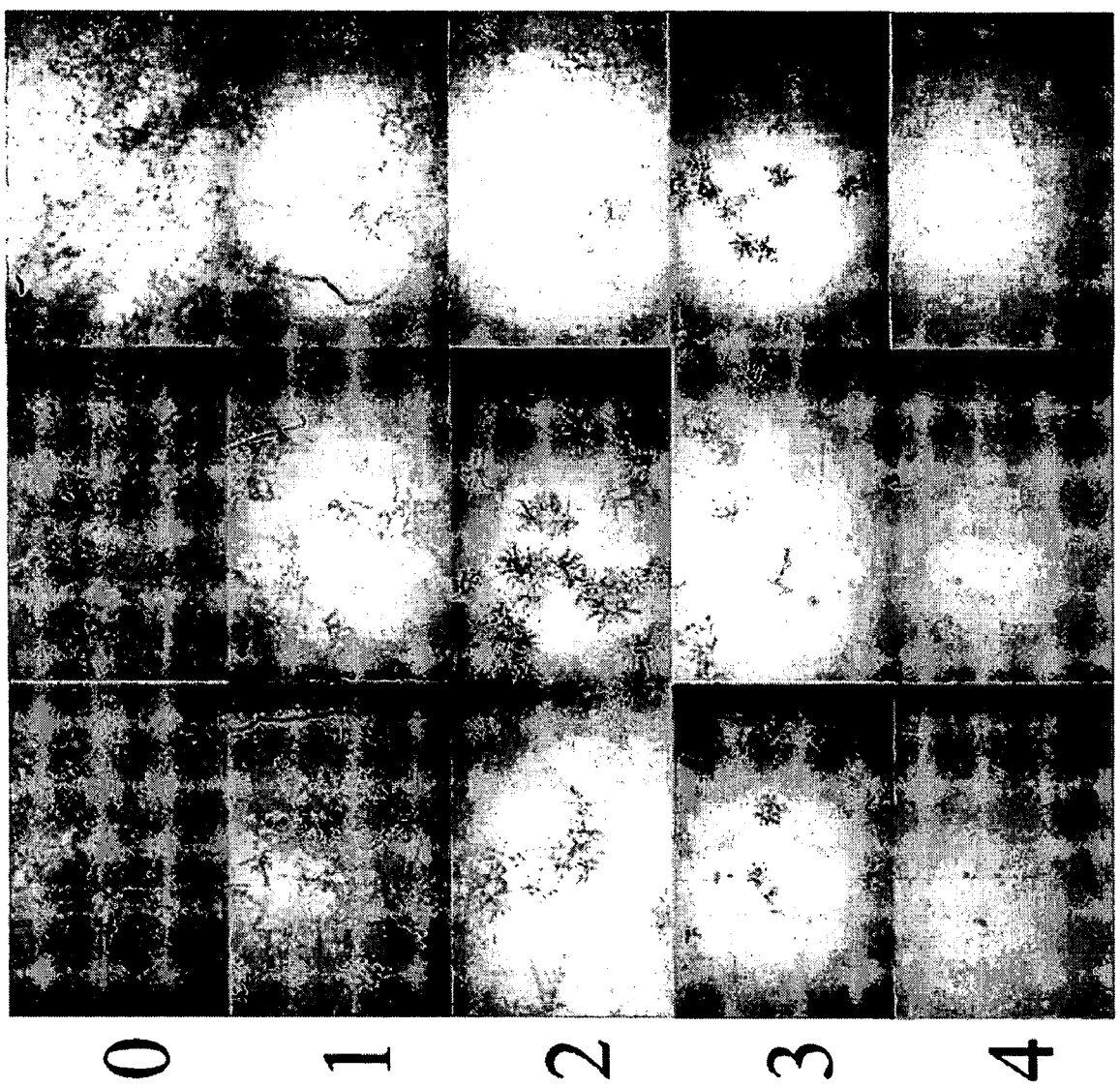
FIG. 3 shows photographic examples of the level of inhibition associated with each numerical score in the antifungal plate assay described in Example 2.

The present invention provides compositions and methods directed to inducing pathogen resistance, particularly fungal resistance, in plants. The compositions are nucleotide and amino acid sequences for antipathogenic polypeptides. Specifically, the present invention provides an antipathogenic polypeptide having the amino acid sequence set forth in SEQ ID NO:1, and variants and fragments thereof, that was isolated from a fungal fermentation broth extract of *Fusarium oxysporum* and designated LB-12265. The fungal strain was isolated from the roots of *Dianthus barbatus L.* in Kiev, Ukraine. Isolated nucleic acid molecules, such as, for example, SEQ ID NO:2, and variants and fragments thereof, comprising nucleotide sequences that encode the amino acid sequence shown in SEQ ID NO:1 are further provided.

Nucleotide sequences that are optimized for expression in plants, particularly maize, and that encode the polypeptide of SEQ ID NO:1 can be generated using standard methods known in the art. Such plant-optimized nucleotide sequences are further encompassed by the present invention. Plants, plant cells, seeds, and microorganisms comprising a nucleotide sequence that encodes an antipathogenic polypeptide of the invention are also disclosed herein. Antipathogenic compositions comprising an isolated antipathogenic, particularly an antifungal, polypeptide or a microorganism that expresses a polypeptide of the invention in combination with a carrier are further provided. The compositions of the invention find use in generating pathogen-resistant plants and in protecting plants from pathogens, particularly fungal pathogens.

The polypeptide disclosed herein in SEQ ID NO:1 displays antifungal activity against fungal plant pathogens, such as, for example, *Colletotrichum graminicola, Diplodia maydis, Fusarium graminearum*, and *Fusarium verticillioides*. The species of origin of the antifungal polypeptide of SEQ ID NO:1 has been determined to be fungal. In particular, the fungal source of polypeptide SEQ ID NO:1 is *Fusarium oxysporum*.

Additional homologs with sequence similarity to the antifungal polypeptide of SEQ ID NO:1 have been identified from other fungal sources. In particular, the deduced amino acid sequence encoded by a nucleotide sequence isolated from a fungal contaminant, most likely a *Fusarium* fungal contaminant, present in a proprietary maize EST library is disclosed herein (amino acid sequence set forth in SEQ ID NO:3; nucleotide sequence set forth in SEQ ID NO:4). This polypeptide has antifungal activity against *Fusarium verticillioides*. Database searches also revealed that SEQ ID NO:1 is homologous to the predicted translation products of a nucleotide sequence isolated from a *F. verticillioides* wild type subtraction library (amino acid sequence set forth in SEQ ID NO:5; nucleotide sequence set forth in SEQ ID NO:6 (GenBank Accession No. CF453104)) and a nucleotide sequence isolated from a *Fusarium sporotrichioides* cDNA library (amino acid sequence set forth in SEQ ID NO:7; nucleotide sequence set forth in SEQ ID NO:8 (GenBank Accession No. BI200659)). Neither the *F. verticillioides* nor the *F. sporotrichioides* nucleotide sequence is reported in the literature to encode an antifungal polypeptide. The antifungal polypeptide of SEQ ID NO:1 also shares homology with a hypothetical protein of unknown function isolated from *Gibberella zeae* (amino acid sequence set forth in SEQ ID NO:9 (Accession No. XP_383079); nucleotide sequence set forth in SEQ ID NO:10 (Accession No. XM_383079)) and a QI74 protein isolated from *Hypocrea lixii* (amino acid sequence set forth in SEQ ID NO:11 (Accession No. CAA64974); nucleotide sequence set forth in SEQ ID NO:12 (Accession No. X95671)). See also Rey et al. (1998) *Proc. Natl. Acad. Sci. USA* 95:6212-6216. Alignments of the amino acid sequences for the predicted mature LB-12265 polypeptide (SEQ ID NO:1) and the predicted full-length (SEQ ID NO:14)

Figures 1, 5:
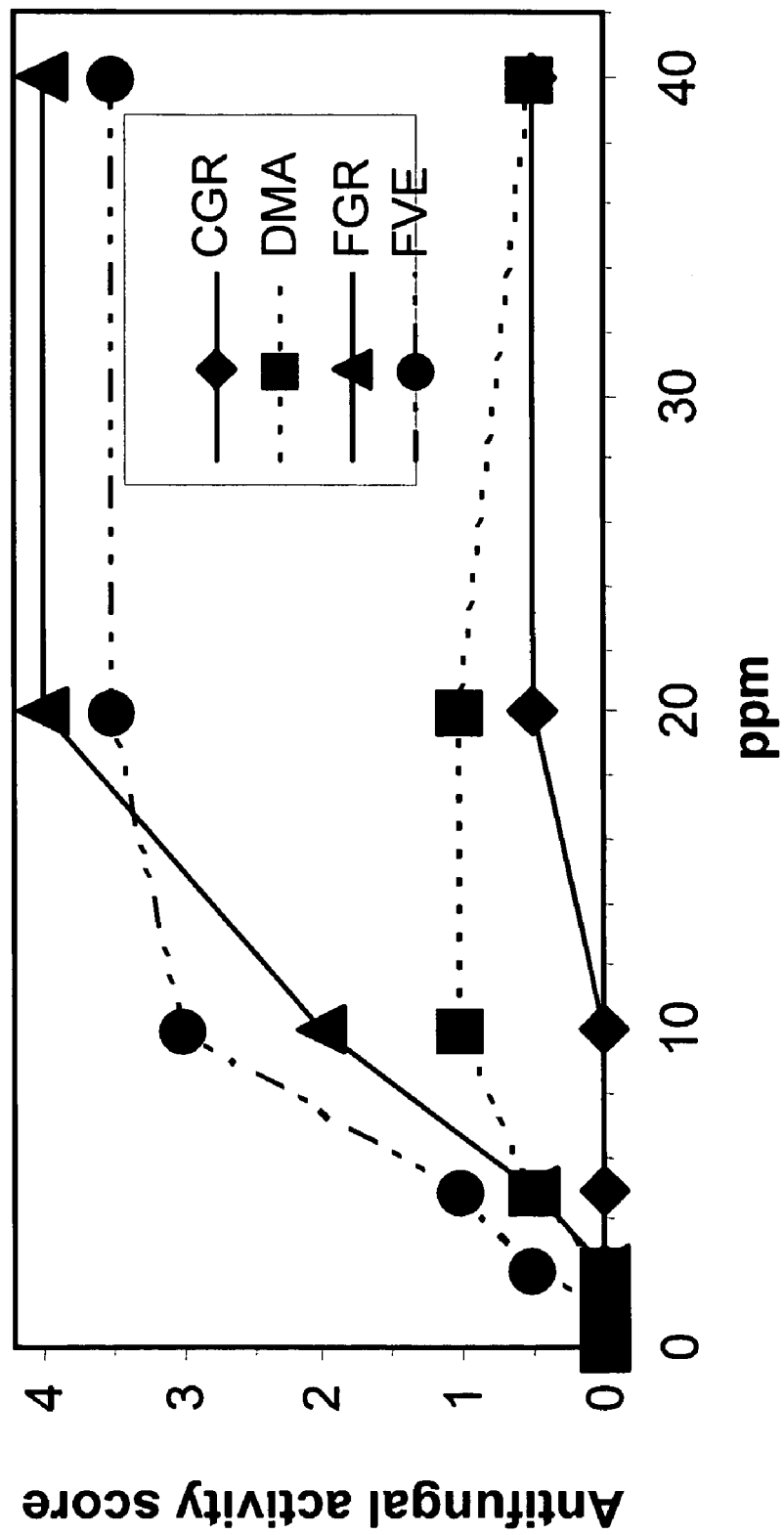
FIG. 1 shows a sequence alignment of the amino acid sequence of the predicted mature peptide of LB-12265 (SEQ ID NO:1) with homologous regions of the polypeptides disclosed in SEQ ID NOs:3,5,7,9, and 11. SEQ ID NO:3 is the deduced amino acid sequence encoded by a nucleotide sequence isolated from a fungal contaminant of a proprietary maize EST library. SEQ ID NO:5 is the predicted translation product of a nucleotide sequence isolated from a *Fusarium verticillioides* wild type subtraction library. SEQ ID NO:7 is the predicted translation product of a nucleotide sequence isolated from a *Fusarium sporotrichioides* cDNA library. SEQ ID NO:9 comprises the amino acid sequence of a hypothetical polypeptide from *Gibberella zeae*. SEQ ID NO:11 comprises the amino acid sequence of a polypeptide from *Hypocrea lixii*.
FIG. 5 provides the results of antifungal activity assays performed with the polypeptides set forth in SEQ ID NO:7, 9, and 11, as described in Example 4. Antifungal activity against *Colletotrichum graminicola, Diplodia maydis, Fusarium graminearum*, and *Fusarium verticillioides* was observed.
Figures 2, 5:
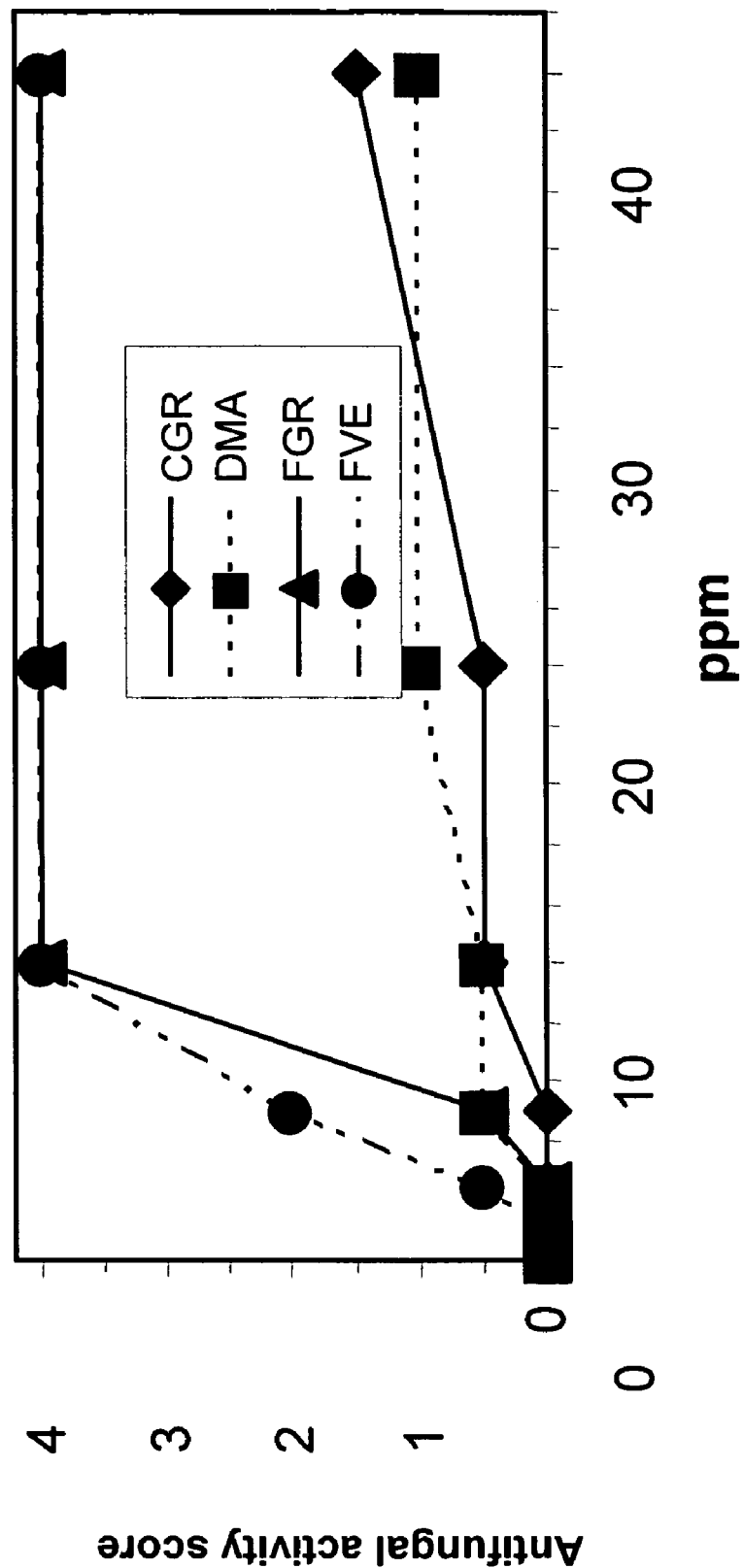
FIG. 2 shows a sequence alignment of the amino acid sequence of the predicted full-length LB-12265 polypeptide (SEQ ID NO:14) with the sequences of SEQ ID NOs:3,5,7,9, and 11 described above. The full-length LB-12265 polypeptide comprises a predicted signal peptide and propeptide region, as described herein below.
Figures 3, 5:
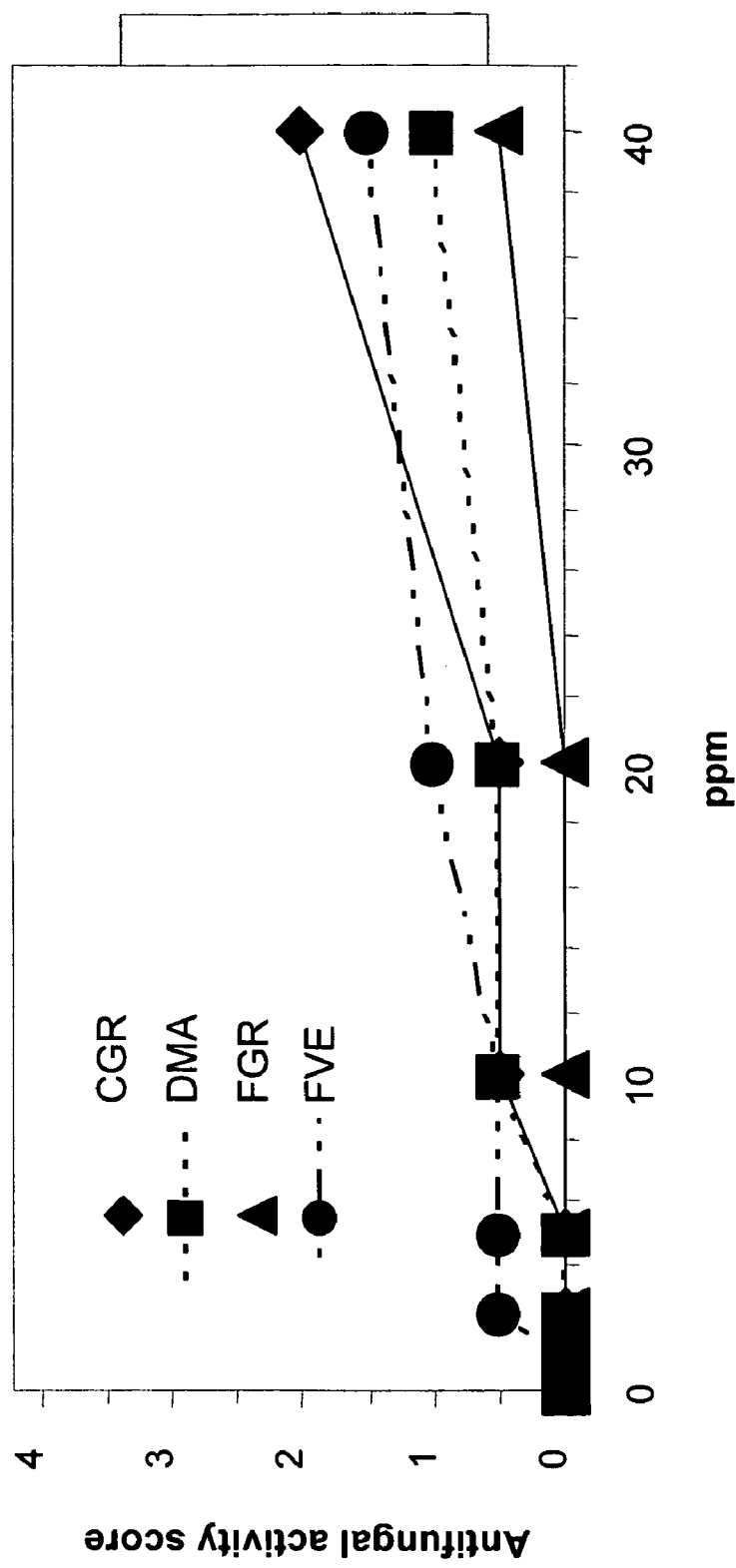

LB-12265 antifungal polypeptide with the above amino acid sequences are provided in FIGS. 1 and 2, respectively. The amino acid sequences set forth in SEQ ID NOs:3, 5, 7, 9, and 11 and the nucleotide sequences set forth in SEQ ID NOs:4, 6, 8, 10, and 12 can be used in the antipathogenic compositions and methods of the invention.

As used herein, "domain" or "antipathogenic polypeptide domain" or any grammatical variation thereof refer to fragments of a full-length antipathogenic polypeptide that possess antipathogenic activity. In the present application, domains of antipathogenic polypeptides that possess antipathogenic activity may be at times referred to simply as "antipathogenic polypeptides." Polypeptides comprising an antipathogenic, more particularly an antifungal, domain, of the invention may display antipathogenic activity despite the presence of additional amino acids. The full-length protein that includes the predicted mature SEQ ID NO:9 peptide is set forth in SEQ ID NO:34 and possesses four domains, designated here as the A (i.e., the predicted mature polypeptide), B, C, and D domains, each of which display antipathogenic activity, more particularly antifungal activity. The A, B, C, and D domains are set forth below and in SEQ ID NOs:9, 35, 36, and 37. The results demonstrating the antipathogenic activity of the B, C, and D domains of SEQ ID NO:34 are presented in FIG. 6, as further explained in Example 5.

```
Full-length polypeptide comprising
SEQ ID NOs: 9, 35, 36, and 37:
MRFSNLFLGAVFAVTSVAAMANPAAEAGSLMERSKH  (SEQ ID NO:34)
HHDCGKHASYNTEKKECVCHVSGETYHKKHHKCKKP
KEDKKHHSRDVLEERSPKKDEHEHCGKHASFNEEKK
ECVCHDKSEVFEKHHKKCKKAKDEKKKDDKHHSRD
VLEERDPKKDKHHDHCGKHASYSEEKKECVCHNKAE
VFERKHKKCKKHISLRSIFNHCGRHAYYDEAKKECI
CHDAGKDFLKKHKTCACPQGEKWHHIERKCKA Domain A of SEQ ID NO:34:
SKHHHDCGKHASYNTEKKECVCHVSGETYHKKHHKC  (SEQ ID NO:9)
KKPKEDKKHHSRDVLE Domain B of SEQ ID NO:34:
SPKKDEHEHCGKHASFNEEKKECVCHDKSEVFEKHH  (SEQ ID NO:35)
KKCKKAKDEKKKDDKKH Domain C of SEQ ID NO:34:
KKDKHHDHCGKHASYSEEKKECVCHNKAEVFERKHK  (SEQ ID NO:36)
KCKKHISLR Domain D of SEQ ID NO:34:
SIFNHCGRHAYYDEAKKECICHDAGKDFLKKHKTCA  (SEQ ID NO:37)
CPQGEKWHHIERKCKA
```

The antipathogenic domain polypeptides find further use in methods for screening for antipathogenic polypeptides, more particularly antifungal polypeptides. Such methods comprise, for example, providing a candidate polypeptide of interest, analyzing the polypeptide for the presence of an antipathogenic domain to identify putative antipathogenic polypeptides, and assaying the putative antipathogenic polypeptide for antipathogenic activity. Methods for determining the presence or absence of a sequence of interest within a polypeptide are routine. As described herein below, assays for assessing antipathogenic activity, particularly antifungal activity are well known in the art. For example, a polypeptide comprising an antipathogenic domain set forth in SEQ ID NO:9, 35, 36, or 37 (i.e., the A, B, C, or D domains of SEQ ID NO:34) may be identified and further analyzed using standard assays to assess the antipathogenic activity of a particular polypeptide. In certain aspects of the invention the antipathogenic activity is antifungal activity.

The nucleic acids and polypeptides of the present invention find use in methods for inducing pathogen resistance in a plant. Accordingly, the compositions and methods disclosed herein are useful in protecting plants against fungal pathogens, viruses, nematodes and the like. "Pathogen resistance" or "disease resistance" is intended to mean that the plant avoids the disease symptoms that are the outcome of plant-pathogen interactions. That is, pathogens are prevented from causing plant diseases and the associated disease symptoms, or alternatively, the disease symptoms caused by the pathogen are minimized or lessened, such as, for example, the reduction of stress and associated yield loss. One of skill in the art will appreciate that the compositions and methods disclosed herein can be used with other compositions and methods available in the art for protecting plants from insect and pathogen attack.

"Antipathogenic compositions" or "antipathogenic polypeptides" or "antipathogenic polypeptide domains" is intended to mean that the compositions of the invention have antipathogenic activity and thus are capable of suppressing, controlling, and/or killing the invading pathogenic organism. An antipathogenic polypeptide of the invention (or domain thereof) will reduce the disease symptoms resulting from pathogen challenge by at least about 5% to about 50%, at least about 10% to about 60%, at least about 30% to about 70%, at least about 40% to about 80%, or at least about 50% to about 90% or greater. Hence, the methods of the invention can be utilized to protect plants from disease, particularly those diseases that are caused by plant pathogens. In particular embodiments, the antipathogenic activity exhibited by the polypeptides (or domain thereof) of the invention is antifungal activity. As used herein, "antifungal activity" refers to the ability to suppress, control, and/or kill the invading fungal pathogen. Likewise, "fungal resistance" refers to enhanced tolerance to a fungal pathogen when compared to that of an untreated or wild type plant. Resistance may vary from a slight increase in tolerance to the effects of the fungal pathogen (e.g., partial inhibition) to total resistance such that the plant is unaffected by the presence of the fungal pathogen. An increased level of resistance against a particular fungal pathogen or against a wider spectrum of fungal pathogens may both constitute antifungal activity or improved fungal resistance.

Assays that measure antipathogenic activity are commonly known in the art, as are methods to quantitate disease resistance in plants following pathogen infection. See, for example, U.S. Pat. No. 5,614,395, herein incorporated by reference. Such techniques include, measuring over time, the average lesion diameter, the pathogen biomass, and the overall percentage of decayed plant tissues. For example, a plant either expressing an antipathogenic polypeptide or having an antipathogenic composition applied to its surface shows a decrease in tissue necrosis (i.e., lesion diameter) or a decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107-15111, herein incorporated by reference.

Furthermore, in vitro antipathogenic assays include, for example, the addition of varying concentrations of the antipathogenic composition to paper disks and placing the disks on agar containing a suspension of the pathogen of interest. Following incubation, clear inhibition zones develop around the discs that contain an effective concentration of the antipathogenic polypeptide (Liu et al. (1994) *Plant Biology* 91:1888-1892, herein incorporated by reference). Additionally, microspectrophotometrical analysis can be used to measure the in vitro antipathogenic properties of a composition (Hu et al. (1997) *Plant Mol. Biol.* 34:949-959 and Cammue et al. (1992) *J. Biol. Chem.* 267: 2228-2233, both of which are herein incorporated by reference). Assays that specifically measure antifungal activity are also well known in the art. See, for example, Duvick et al. (1992) *J. Biol. Chem.* 267: 18814-18820; Lacadena et al. (1995) *Arch. Biochem. Biophys.* 324:273-281; Xu et al. (1997) *Plant Mol. Biol.* 34: 949-959; Lee et al. (1999) *Biochem. Biophys. Res. Comm.* 263:646-651; Vila et al. (2001) *Mol. Plant Microbe Interact.* 14:1327-1331; Moreno et al. (2003) *Phytpathol.* 93:1344-1353; Kaiserer et al. (2003) *Arch. Microbiol.* 180:204-210; and U.S. Pat. No. 6,015,941.

The compositions disclosed herein comprise isolated nucleic acids that encode antipathogenic polypeptides, expression cassettes comprising the nucleotide sequences of the invention, and isolated antipathogenic polypeptides. Antipathogenic compositions comprising a polypeptide of the invention in combination with a carrier are also provided. The invention further discloses plants and microorganisms transformed with nucleic acids that encode antipathogenic proteins. The compositions find use in methods for inducing pathogen resistance in a plant and for protecting a plant from a pathogen, particularly fungal pathogens.

In particular aspects, methods for inducing pathogen resistance in a plant comprise introducing into a plant at least one expression cassette, wherein the expression cassette comprises a nucleotide sequence encoding an antipathogenic polypeptide of the invention operably linked to a promoter that drives expression in the plant. The plant expresses the antipathogenic polypeptide, thereby exposing the pathogen to the polypeptide at the site of pathogen attack. In particular embodiments, the polypeptide has antifungal activity, and the pathogen is a fungus, such as, for example, *Colletotrichum graminicola*, *Diplodia maydis*, *Fusarium graminearum*, or *Fusarium verticillioides*. Expression of an antipathogenic polypeptide of the invention (or antipathogenic polypeptide domain) may be targeted to specific plant tissues where pathogen resistance is particularly important, such as, for example, the leaves, roots, stalks, or vascular tissues. Such tissue-preferred expression may be accomplished by root-preferred, leaf-preferred, vascular tissue-preferred, stalk-preferred, or seed-preferred promoters. Moreover, the polypeptides of the invention may also be targeted to specific subcellular locations within a plant cell or, alternatively, secreted from the cell, as described herein below.

Just as expression of an antipathogenic polypeptide of the invention may be targeted to specific plant tissues or cell types through the use of appropriate promoters, it may also be targeted to different locations within the cell through the use of targeting information or "targeting labels." Unlike the promoter, which acts at the transcriptional level, such targeting information is part of the initial translation product. Depending on the mode of infection of the pathogen or the metabolic function of the tissue or cell type, the location of the protein in different compartments of the cell may make it more efficacious against a given pathogen or make it interfere less with the functions of the cell. For example, one may produce a protein preceded by a signal peptide, which directs the translation product into the endoplasmic reticulum, by including in the construct (i.e. expression cassette) sequences encoding a signal peptide (such sequences may also be called the "signal sequence"). The signal sequence used could be, for example, one associated with the gene encoding the polypeptide, or it may be taken from another gene. There are many signal peptides described in the literature, and they are largely interchangeable (Raikhel and Chrispeels, "Protein sorting and vesicle traffic" in Buchanan et al., eds, (2000) *Biochemistry and Molecular Biology of Plants* (American Society of Plant Physiologists, Rockville, Md.), herein incorporated by reference). The addition of a signal peptide will result in the translation product entering the endoplasmic reticulum (in the process of which the signal peptide itself is removed from the polypeptide), but the final intracellular location of the protein depends on other factors, which may be manipulated to result in localization most appropriate for the pathogen and cell type. The default pathway, that is, the pathway taken by the polypeptide if no other targeting labels are included, results in secretion of the polypeptide across the cell membrane (Raikhel and Chrispeels, supra) into the apoplast. The apoplast is the region outside the plasma membrane system and includes cell walls, intercellular spaces, and the xylem vessels that form a continuous, permeable system through which water and solutes may move. This will often be a suitable location. In particular embodiments, a nucleotide sequence encoding a barley alpha-amylase (BAA) signal peptide is joined in frame with a polynucleotide of the invention. The nucleotide sequence encoding the BAA signal peptide and the amino acid sequence for the BAA signal peptide are set forth in SEQ ID NO:15 and SEQ ID NO:16, respectively. An exemplary nucleotide sequence encoding the BAA signal peptide joined with a nucleotide sequence encoding SEQ ID NO:1 and the amino acid sequence for BAA-SEQ ID NO:1 are provided in SEQ ID NO:17 and SEQ ID NO:18, respectively.

Other pathogens may be more effectively combated by locating the peptide within the cell rather than outside the cell membrane. This can be accomplished, for example, by adding an endoplasmic reticulum retention signal encoding sequence to the sequence of the gene. Methods and sequences for doing this are described in Raikhel and Chrispeels, supra; for example, adding sequences encoding the amino acids K, D, E and L in that order, or variations thereof described in the literature, to the end of the protein coding portion of the polypeptide will accomplish this. ER retention sequences are well known in the art and include, for example, KDEL (SEQ ID NO:19), SEKDEL (SEQ ID NO:20), HDEL (SEQ ID NO:21), and HDEF (SEQ ID NO:22). See, for example, Denecke et al. (1992). *EMBO J.* 11:2345-2355; Wandelt et al. (1992) *Plant J.* 2:181-192; Denecke et al. (1993) *J. Exp. Bot.* 44:213-221; Vitale et al. (1993) *J. Exp. Bot.* 44:1417-1444; Gomord et al. (1996) *Plant Physiol. Biochem.* 34:165-181; Lehmann et al. (2001) *Plant Physiol.* 127 (2): 436-449.

Alternatively, the use of vacuolar targeting labels such as those described by Raikhel and Chrispeels, supra, in addition to a signal peptide will result in localization of the peptide in a vacuolar structure. As described in Raikhel and Chrispeels, supra, the vacuolar targeting label may be placed in different positions in the construct. Use of a plastid transit peptide encoding sequence instead of a signal peptide encoding sequence will result in localization of the polypeptide in the plastid of the cell type chosen (Raikhel and Chrispeels, supra). Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:

1414-1421; and Shah et al. (1986) *Science* 233:478-481. Chloroplast targeting sequences that encode such transit peptides are also known in the art and include the chloroplast small subunit of ribulose-1,5-bisphosphate carboxylase (Rubisco) (de Castro Silva Filho et al. (1996) *Plant Mol. Biol.* 30:769-780; Schnell et al. (1991) *J. Biol. Chem.* 266(5):3335-3342); 5-(enolpyruvyl)shikimate-3-phosphate synthase (EPSPS) (Archer et al. (1990) *J. Bioenerg. Biomemb.* 22(6): 789-810); tryptophan synthase (Zhao et al. (1995) *J. Biol. Chem.* 270(11):6081-6087); plastocyanin (Lawrence et al. (1997) *J. Biol. Chem.* 272(33):20357-20363); chorismate synthase (Schmidt et al. (1993) *J. Biol. Chem.* 268(36): 27447-27457); and the light harvesting chlorophyll a/b binding protein (LHBP) (Lamppa et al. (1988) *J. Biol. Chem.* 263:14996-14999). A person skilled in the art could also envision generating transgenic plants in which the chloroplasts have been transformed to overexpress a gene for an antipathogenic peptide. See, for example, Daniell (1999) *Nature Biotech* 17:855-856; and U.S. Pat. No. 6,338,168.

One could also envision localizing the antipathogenic polypeptide, or domain thereof, in other cellular compartments by addition of suitable targeting information. (Raikhel and Chrispeels, supra). A useful site available on the world wide web that provides information and references regarding recognition of the various targeting sequences can be found at: psort.nibb.ac.jp/mit. Other references regarding the state of the art of protein targeting include Silva-Filho (2003) *Curr. Opin. Plant Biol.* 6:589-595; Nicchitta (2002) *Curr. Opin. Cell Biol.* 14:412-416; Bruce (2001) *Biochim Biophys Acta* 1541: 2-21; Hadlington & Denecke (2000) *Curr. Opin. Plant Biol.* 3: 461-468; Emanuelsson et al. (2000) *J Mol. Biol.* 300: 1005-1016; Emanuelsson & von Heijne (2001) *Biochim Biophys Acta* 1541: 114-119, herein incorporated by reference.

The compositions of the invention find further use in methods directed to protecting a plant from a pathogen. "Protecting a plant from a pathogen" is intended to mean killing the pathogen or preventing or limiting disease formation on a plant. In some embodiments, an antipathogenic composition comprising an antipathogenic polypeptide and a carrier is applied directly to the environment of a plant pathogen, such as, for example, on a plant or in the soil or other growth medium surrounding the roots of the plant, in order to protect the plant from pathogen attack. Transformed microorganisms comprising a nucleotide sequence encoding an antipathogenic protein of the invention (or antipathogenic domain thereof) and methods of using them to protect a plant from a pathogen are further provided. In some embodiments, the transformed microorganism is applied directly to a plant or to the soil in which a plant grows.

As used herein, "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. Polypeptides of the invention can be produced either from a nucleic acid disclosed herein, or by the use of standard molecular biology techniques. For example, a truncated protein of the invention can be produced by expression of a recombinant nucleic acid of the invention in an appropriate host cell, or alternatively by a combination of ex vivo procedures, such as protease digestion and purification.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Fragments and variants of the disclosed nucleotide sequences and proteins encoded thereby are also encompassed by the present invention. "Fragment" is intended to mean a portion of the nucleotide sequence or a portion of the amino acid sequence and hence protein encoded thereby. Fragments of a nucleotide sequence may encode protein fragments that retain the biological activity of the native protein and hence have antipathogenic activity, more particularly antifungal activity. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the polypeptides of the invention.

A fragment of a nucleotide sequence that encodes a biologically active portion of an antifungal polypeptide of the invention will encode at least 15, 25, 30, 40, or 50 contiguous amino acids, or up to the total number of amino acids present in a full-length antifungal polypeptide of the invention (for example, 52 amino acids for SEQ ID NO:1). Fragments of a nucleotide sequence that are useful as hybridization probes or PCR primers generally need not encode a biologically active portion of an antipathogenic protein.

As used herein, "full-length sequence" in reference to a specified polynucleotide means having the entire nucleic acid sequence of a native sequence. "Native sequence" is intended to mean an endogenous sequence, i.e., a non-engineered sequence found in an organism's genome.

Thus, a fragment of a nucleotide sequence of the invention may encode a biologically active portion of an antipathogenic polypeptide, or it may be a fragment that can be used as a hybridization probe or PCR primer using methods disclosed below. A biologically active portion of an antipathogenic polypeptide can be prepared by isolating a portion of one of the nucleotide sequences of the invention, expressing the encoded portion of the antipathogenic protein (e.g., by recombinant expression in vitro), and assessing the activity of the encoded portion of the antifungal protein. Nucleic acid molecules that are fragments of a nucleotide sequence of the invention comprise at least 15, 20, 50, 75, 100, or 150 contiguous nucleotides, or up to the number of nucleotides present in a full-length nucleotide sequence disclosed herein.

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. One of skill in the art will recognize that variants of the nucleic acids of the invention will be constructed such that the open reading frame is maintained. For polynucleotides, conservative variants include those sequences that, because of the degeneracy of the genetic code, encode the amino acid sequence of one of the antipathogenic polypeptides of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotide, such as those generated, for example, by using site-directed mutagenesis but which still encode an antipathogenic protein of the invention. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide of SEQ ID NO:1 is disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the present invention are biologically active, that is they continue to possess the desired biological activity of the native protein, that is, antipathogenic, particularly antifungal, activity as described herein. Such variants may result from, for example, genetic polymorphism or from human manipulation. Biologically active variants of a native antipathogenic protein of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants and fragments of the antipathogenic proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154: 367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the invention include both the naturally occurring sequences as well as mutant forms. Likewise, the proteins of the invention encompass naturally occurring proteins as well as variations and modified forms thereof. Such variants will continue to possess the desired antipathogenic, particularly antifungal, activity. Obviously, the mutations that will be made in the DNA encoding the variant must not place the sequence out of reading frame and optimally will not create complementary regions that could produce secondary mRNA structure. See, EP Patent No. 0075444.

In nature, some polypeptides are produced as complex precursors which, in addition to targeting labels such as the signal peptides discussed elsewhere in this application, also contain other fragments of peptides which are removed (processed) at some point during protein maturation, resulting in a mature form of the polypeptide that is different from the primary translation product (aside from the removal of the signal peptide). "Mature protein" refers to a post-translationally processed polypeptide; i.e., one from which any pre- or propeptides present in the primary translation product have been removed. "Precursor protein" or "prepropeptide" or "preproprotein" all refer to the primary product of translation of mRNA; i.e., with pre- and propeptides still present. Pre- and propeptides may include, but are not limited to, intracellular localization signals. "Pre" in this nomenclature generally refers to the signal peptide. The form of the translation product with only the signal peptide removed but no further processing yet is called a "propeptide" or "proprotein." The fragments or segments to be removed may themselves also be referred to as "propeptides." A proprotein or propeptide thus has had the signal peptide removed, but contains propeptides (here referring to propeptide segments) and the portions that will make up the mature protein. The skilled artisan is able to determine, depending on the species in which the proteins are being expressed and the desired intracellular location, if higher expression levels might be obtained by using a gene construct encoding just the mature form of the protein, the mature form with a signal peptide, or the proprotein (i.e., a form including propeptides) with a signal peptide. For optimal expression in plants or fungi, the pre- and propeptide sequences may be needed. The propeptide segments may play a role in aiding correct peptide folding.

The genomic sequence of the full-length LB-12265 polypeptide is provided in SEQ ID NO:13. The full-length LB-12265 polypeptide sequence contains a predicted signal peptide and propeptide region and is set forth is SEQ ID NO:14. The genomic sequence of the full-length cr1n.pk0189.g4 polypeptide is provided in SEQ ID NO:23. The full-length cr1n.pk0189.g4 polypeptide sequence contains a predicted signal peptide and propeptide region and is set forth is SEQ ID NO:24. Experimental details regarding isolation of the LB-12265 and cr1n.pk0189.g4 genes are provided in Example 3 below.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by assays that measure antipathogenic activity such as antifungal plate assays. See, for example, Duvick et al. (1992) *J. Biol. Chem.* 267:18841-18820, herein incorporated by reference.

Variant polynucleotides and proteins also encompass sequences and proteins derived from a mutagenic and recombinogenic procedure such as DNA shuffling. With such a procedure, one or more different antipathogenic protein coding sequences can be manipulated to create a new antipathogenic protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the antipathogenic protein gene of the invention and other known antipathogenic protein genes to obtain a new gene coding for a protein with an improved property of interest, such as increased antifungal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272: 336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The polynucleotides of the invention can be used to isolate corresponding sequences from other organisms, particularly other microorganisms, more particularly other fungi. In this manner, methods such as PCR, hybridization, and the like can be used to identify such sequences based on their sequence homology to the sequences set forth herein. Sequences isolated based on their sequence identity to the entire sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that encode for an antipathogenic, particularly antifungal, protein and which hybridize under stringent conditions to the sequences disclosed herein, or to variants or fragments thereof, are encompassed by the present invention.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the polynucleotides of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire polynucleotide disclosed herein, or one or more portions thereof, may be used as a probe capable of specifically hybridizing to corresponding polynucleotides and messenger RNAs. To achieve specific hybridization under a variety of conditions, such probes include sequences that are unique among antipathogenic polynucleotide sequences and are optimally at least about 10 nucleotides in length, and most optimally at least about 20 nucleotides in length. Such probes may be used to amplify corresponding polynucleotides from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. "Stringent conditions" or "stringent hybridization conditions" is intended to mean conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the thermal melting point ($T_m$) can be approximated from the equation of Meinkoth and Wahl (1984) *Anal. Biochem.* 138: 267-284: $T_m=81.5°$ C.$+16.6$ (log M)$+0.41$ (% GC)$-0.61$ (% form)$-500$/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

The following terms are used to describe the sequence relationships between two or more polynucleotides or polypeptides: (a) "reference sequence", (b) "comparison window", (c) "sequence identity", and, (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J. Mol. Biol.* 48:443-453; the search-for-local-alignment method of Pearson and Lipman (1988) *Proc. Natl. Acad. Sci.* 85:2444-2448; the algorithm of Karlin and Altschul (1990) *Proc. Natl. Acad. Sci. USA* 872264, modified as in Karlin and Altschul (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA). Alignments using these programs can be performed using the default parameters. The CLUSTAL program is well described by Higgins et al. (1988) *Gene* 73:237-244 (1988); Higgins et al. (1989) *CABIOS* 5:151-153; Corpet et al. (1988) *Nucleic Acids Res.* 16:10881-90; Huang et al. (1992) *CABIOS* 8:155-65; and Pearson et al. (1994) *Meth. Mol. Biol.* 24:307-331. The ALIGN program is based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. "Equivalent program" is intended to mean any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, and the like.

In some embodiments, expression cassettes comprising a promoter operably linked to a heterologous nucleotide sequence of the invention that encodes an antipathogenic polypeptide are further provided. The expression cassettes of the invention find use in generating transformed plants, plant cells, and microorganisms and in practicing the methods for inducing pathogen resistance disclosed herein. The expression cassette will include 5' and 3' regulatory sequences operably linked to a polynucleotide of the invention. "Operably linked" is intended to mean a functional linkage between two or more elements. For example, an operable linkage between a polynucleotide of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide that encodes an antipathogenic polypeptide to be under the transcriptional regulation of the regulatory regions. The expression cassette may additionally contain selectable marker genes.

The expression cassette will include in the 5'-3' direction of transcription, a transcriptional initiation region (i.e., a promoter), translational initiation region, a polynucleotide of the invention, a translational termination region and, optionally, a transcriptional termination region functional in the host organism. The regulatory regions (i.e., promoters, transcriptional regulatory regions, and translational termination regions) and/or the polynucleotide of the invention may be native/analogous to the host cell or to each other. Alternatively, the regulatory regions and/or the polynucleotide of the invention may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The optionally included termination region may be native with the transcriptional initiation region, may be native with the operably linked polynucleotide of interest, may be native with the plant host, or may be derived from another source (i.e., foreign or heterologous) to the promoter, the polynucleotide of interest, the host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639. In particular embodiments, the potato protease inhibitor II gene (PinII) terminator is used. See, for example, Keil et al. (1986) *Nucl. Acids Res.* 14:5641-5650; and An et al. (1989) *Plant Cell* 1:115-122, herein incorporated by reference in their entirety.

Where appropriate, the polynucleotides may be optimized for increased expression in the transformed organism. For example, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, N.Y.), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al (1992) *Cell* 71:63-72; Reznikoff (1992) *Mol Microbiol.* 6:2419-2422; Barkley et al. (1980) in *The Operon*, pp. 177-220; Hu et al. (1987) *Cell* 48:555-566; Brown et al (1987) *Cell* 49:603-612; Figge et al. (1988) *Cell* 52:713-722; Deuschle et al (1989) *Proc. Natl. Acad. Aci. USA* 86:5400-5404; Fuerst et al (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al (1992) *Proc. Natl. Acad. Sci. USA* 89:5547-5551; Oliva et al. (1992) *Antimicrob. Agents Chemother.* 36:913-919; Hlavka et al (1985) *Handbook of Experimental Pharmacology*, Vol. 78

(Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

A number of promoters can be used in the practice of the invention, including the native promoter of the polynucleotide sequence of interest. The promoters can be selected based on the desired outcome. A wide range of plant promoters are discussed in the recent review of Potenza et al. (2004) *In Vitro Cell Dev Biol—Plant* 40:1-22, herein incorporated by reference. For example, the nucleic acids can be combined with constitutive, tissue-preferred, pathogen-inducible, or other promoters for expression in plants. Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611. In particular embodiments, the E35S-Ubi promoter is used for strong constitutive expression.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol.* 89:245-254; Uknes et al. (1992) *Plant Cell* 4:645-656; and Van Loon (1985) *Plant Mol. Virol.* 4:111-116. See also WO 99/43819, herein incorporated by reference.

Of interest are promoters that result in expression of a protein locally at or near the site of pathogen infection. See, for example, Marineau et al. (1987) *Plant Mol. Biol.* 9:335-342; Matton et al. (1989) *Molecular Plant-Microbe Interactions* 2:325-331; Somsisch et al. (1986) *Proc. Natl. Acad. Sci. USA* 83:2427-2430; Somsisch et al. (1988) *Mol. Gen. Genet.* 2:93-98; and Yang (1996) *Proc. Natl. Acad. Sci. USA* 93:14972-14977. See also, Chen et al. (1996) *Plant J.* 10:955-966; Zhang et al. (1994) *Proc. Natl. Acad. Sci. USA* 91:2507-2511; Warner et al. (1993) *Plant J.* 3:191-201; Siebertz et al. (1989) *Plant Cell* 1:961-968; U.S. Pat. No. 5,750,386 (nematode-inducible); and the references cited therein. Of particular interest are the inducible promoter for the maize PRms gene, whose expression is induced by the pathogen *Fusarium moniliforme* (see, for example, Cordero et al. (1992) *Physiol. Mol. Plant Path.* 41:189-200) and the inducible maize promoters described in U.S. Pat. Nos. 6,429,362 (e.g., Zm-PR1-81 and Zm-PR1-83 promoters), all of which are herein incorporated by reference in their entirety. The promoters described in U.S. Pat. No. 6,720,480, such as the Zm-BBl1 promoter, may also be used in the practice of the invention.

Additionally, as pathogens find entry into plants through wounds or insect damage, a wound-inducible promoter may be used in the constructions of the invention. Such wound-inducible promoters include potato proteinase inhibitor (pin II) gene (Ryan (1990) *Ann. Rev. Phytopath.* 28:425-449; Duan et al. (1996) *Nature Biotechnology* 14:494-498); wun1 and wun2, U.S. Pat. No. 5,428,148; win1 and win2 (Stanford et al. (1989) *Mol. Gen. Genet.* 215:200-208); systemin (McGurl et al. (1992) *Science* 225:1570-1573); WIP1 (Rohmeier et al. (1993) *Plant Mol. Biol.* 22:783-792; Eckelkamp et al. (1993) *FEBS Letters* 323:73-76); MPI gene (Corderok et al. (1994) *Plant J.* 6(2):141-150); and the like, herein incorporated by reference.

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Tissue-preferred promoters can be utilized to target enhanced expression of the antipathogenic polypeptides of the invention within a particular plant tissue. For example, a tissue-preferred promoter may be used to express an antifungal polypeptide in a plant tissue where disease resistance is particularly important, such as, for example, the roots or the leaves. Tissue-preferred promoters include Yamamoto et al. (1997) *Plant J.* 12(2):255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2): 157-168; Rinehart et al. (1996) *Plant Physiol.* 112(3): 1331-1341; Van Camp et al. (1996) *Plant Physiol.* 112(2): 525-535; Canevascini et al. (1996) *Plant Physiol.* 112(2): 513-524; Yamamoto et al. (1994) *Plant Cell Physiol.* 35(5): 773-778; Lam (1994) *Results Probl. Cell Differ.* 20:181-196; Orozco et al. (1993) *Plant Mol Biol.* 23(6):1129-1138; Matsuoka et al. (1993) *Proc Natl. Acad. Sci. USA* 90(20):9586-9590; and Guevara-Garcia et al. (1993) *Plant J.* 4(3):495-505. Such promoters can be modified, if necessary, for weak expression.

Vascular tissue-preferred promoters are known in the art and include those promoters that selectively drive protein expression in, for example, xylem and phloem tissue. Vascular tissue-preferred promoters include, but are not limited to, the *Prunus serotina* prunasin hydrolase gene promoter (see, e.g., International Publication No. WO 03/006651), and also those found in U.S. patent application Ser. No. 10/109,488.

Stalk-preferred promoters may be used to drive expression of an antipathogenic polypeptide of the invention. Exemplary stalk-preferred promoters include the maize MS8-15 gene promoter (see, for example, U.S. Pat. No. 5,986,174 and International Publication No. WO 98/00533), and those found in Graham et al. (1997) *Plant Mol Biol* 33(4): 729-735. In certain embodiments of the invention, the Zm-419 promoter is used for tissue preferred-expression in maize stalk tissue. See, for example, U.S. Provisional Application No. 60/729,772, entitled "Promoter Active at High Levels in Stalks, Stalk Nodes, Roots and Leaf Sheaths," filed Oct. 24, 2005, which is herein incorporated by reference in its entirety.

Leaf-preferred promoters are known in the art. See, for example, Yamamoto et al. (1997) *Plant J.* 12(2):255-265; Kwon et al. (1994) *Plant Physiol.* 105:357-67; Yamamoto et al. (1994) *Plant Cell Physiol.* 35(5):773-778; Gotor et al. (1993) *Plant J.* 3:509-18; Orozco et al. (1993) *Plant Mol. Biol.* 23(6):1129-1138; and Matsuoka et al. (1993) *Proc. Natl. Acad. Sci. USA* 90(20):9586-9590.

Root-preferred promoters are known and can be selected from the many available from the literature or isolated de novo from various compatible species. See, for example, Hire et al. (1992) *Plant Mol. Biol.* 20(2):207-218 (soybean root-specific glutamine synthetase gene); Keller and Baumgartner (1991) *Plant Cell* 3(10):1051-1061 (root-specific control element in the GRP 1.8 gene of French bean); Sanger et al. (1990) *Plant Mol. Biol.* 14(3):433-443 (root-specific promoter of the mannopine synthase (MAS) gene of *Agrobacterium tumefaciens*); and Miao et al. (1991) *Plant Cell* 3(1): 11-22 (full-length cDNA clone encoding cytosolic glutamine synthetase (GS), which is expressed in roots and root nodules of soybean). See also Bogusz et al. (1990) *Plant Cell* 2(7): 633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi (1991) describe their analysis of the promoters of the highly expressed rolC and rolD root-inducing genes of *Agrobacterium rhizogenes* (see *Plant Science* (Limerick) 79(1):69-76). They concluded that enhancer and tissue-preferred DNA determinants are dissociated in those promoters. Teeri et al. (1989) used gene fusion to lacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see *EMBO J.* 8(2):343-350). The TR1' gene, fused to nptII (neomycin phosphotransferase II) showed similar characteristics. Additional root-preferred promoters include the VfENOD-GRP3 gene promoter (Kuster et al. (1995) *Plant Mol. Biol.* 29(4):759-772); and rolB promoter (Capana et al. (1994) *Plant Mol. Biol.* 25(4):681-691. See also U.S. Pat. Nos. 5,837,876; 5,750,386; 5,633,363; 5,459,252; 5,401,836; 5,110,732; and 5,023,179.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10: 108, herein incorporated by reference. Such seed-preferred promoters include, but are not limited to, Cim1 (cytokinin-induced message); cZ19B1 (maize 19 kDa zein); milps (myo-inositol-1-phosphate synthase) (see WO 00/11177 and U.S. Pat. No. 6,225,529; herein incorporated by reference). Gamma-zein is an endosperm-specific promoter. Globulin 1 (Glb-1) is a representative embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, gamma-zein, waxy, shrunken 1, shrunken 2, Globulin 1, etc. See also WO 00/12733, where seed-preferred promoters from end1 and end2 genes are disclosed; herein incorporated by reference.

In certain embodiments the nucleic acid sequences of the present invention can be stacked with any combination of polynucleotide sequences of interest in order to create plants with a desired phenotype. For example, the polynucleotides of the present invention may be stacked with other antifungal genes and the like. The combinations generated can also include multiple copies of any one of the polynucleotides of interest. The polynucleotides of the present invention can also be stacked with any other gene or combination of genes to produce plants with a variety of desired trait combinations including but not limited to traits desirable for animal feed such as high oil genes (e.g., U.S. Pat. No. 6,232,529); balanced amino acids (e.g. hordothionins (U.S. Pat. Nos. 5,990, 389; 5,885,801; 5,885,802; and 5,703,409); barley high lysine (Williamson et al. (1987) *Eur. J. Biochem.* 165:99-106; and WO 98/20122); and high methionine proteins (Pedersen et al. (1986) *J. Biol. Chem.* 261:6279; Kirihara et al. (1988) *Gene* 71:359; and Musumura et al. (1989) *Plant Mol. Biol.* 12: 123)); increased digestibility (e.g., modified storage proteins (U.S. application Ser. No. 10/053,410, filed Nov. 7, 2001); and thioredoxins (U.S. application Ser. No. 10/005, 429, filed Dec. 3, 2001)), the disclosures of which are herein incorporated by reference. The polynucleotides of the present invention can also be stacked with traits desirable for insect, disease or herbicide resistance (e.g., *Bacillus thuringiensis* toxic proteins (U.S. Pat. Nos. 5,366,892; 5,747,450; 5,737, 514; 5,723,756; 5,593,881; Geiser et al (1986) *Gene* 48:109); lectins (Van Damme et al. (1994) *Plant Mol. Biol.* 24:825); fumonisin detoxification genes (U.S. Pat. No. 5,792,931); a virulence and disease resistance genes (Jones et al. (1994) *Science* 266:789; Martin et al. (1993) *Science* 262:1432; Mindrinos et al. (1994) *Cell* 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS genes, GAT genes such as those disclosed in U.S. Patent Application Publication US2004/0082770, also WO02/36782 and WO03/092360)); and traits desirable for processing or process products such as high oil (e.g., U.S. Pat. No. 6,232,529 ); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE) and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)), the disclosures of which are herein incorporated by reference. One could also combine the polynucleotides of the present invention with polynucleotides providing agronomic traits such as male sterility (e.g., see U.S. Pat. No. 5,583,210), stalk strength, flowering time, or transformation technology traits such as cell cycle regulation or gene targeting (e.g. WO 99/61619; WO 00/17364; WO 99/25821), the disclosures of which are herein incorporated by reference.

These stacked combinations can be created by any method including but not limited to cross breeding plants by any conventional or TopCross® methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes.

For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855, and WO99/25853, all of which are herein incorporated by reference.

The methods of the invention involve introducing a polypeptide or polynucleotide into a plant. "Introducing" is intended to mean presenting to the plant the polynucleotide. In some embodiments, the polynucleotide will be presented in such a manner that the sequence gains access to the interior of a cell of the plant, including its potential insertion into the genome of a plant. The methods of the invention do not depend on a particular method for introducing a sequence into a plant, only that the polynucleotide gains access to the interior of at least one cell of the plant. Methods for introducing polynucleotides into plants are known in the art including, but not limited to, stable transformation methods, transient transformation methods, and virus-mediated methods. Polypeptides can also be introduced to a plant in such a manner that they gain access to the interior of the plant cell or remain external to the cell but in close contact with it.

"Stable transformation" is intended to mean that the nucleotide construct introduced into a plant integrates into the genome of the plant and is capable of being inherited by the progeny thereof. "Transient transformation" or "transient expression" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. Nos. 5,563,055 and 5,981,840), direct gene transfer (Paszkowski et al. (1984) *EMBO J.* 3:2717-2722), and ballistic particle acceleration (see, for example, Sanford et al., U.S. Pat. Nos. 4,945,050; 5,879,918; 5,886,244; and 5,932,782; Tomes et al. (1995) in *Plant Cell, Tissue, and Organ Culture: Fundamental Methods*, ed. Gamborg and Phillips (Springer-Verlag, Berlin); McCabe et al. (1988) *Biotechnology* 6:923-926); and Lec1 transformation (WO 00/28058). Also see Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); U.S. Pat. Nos. 5,240,855; 5,322,783 and 5,324,646; Klein et al. (1988) *Plant Physiol.* 91:440-444 (maize); Fromm et al. (1990) *Biotechnology* 8:833-839 (maize); Hooykaas-Van Slogteren et al. (1984) *Nature* (London) 311:763-764; U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, N.Y.), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

In specific embodiments, the antipathogenic sequences of the invention can be provided to a plant using a variety of transient transformation methods. Such transient transformation methods include, but are not limited to, the introduction of the antipathogenic protein or variants and fragments thereof directly into the plant or the introduction of the antipathogenic protein transcript into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it's released to become integrated into the genome is greatly reduced. Such methods include the use particles coated with polyethylimine (PEI; Sigma #P3143).

In other embodiments, the polynucleotide of the invention may be introduced into plants by contacting plants with a virus or viral nucleic acids. Generally, such methods involve incorporating a nucleotide construct of the invention within a viral DNA or RNA molecule. It is recognized that the an antipathogenic polypeptide of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931, and Porta et al. (1996) Molecular *Biotechnology* 5:209-221; herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in transfer cassette flanked by two non-recombinogenic recombination sites. The transfer cassette is introduced into a plant that has stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Pedigree breeding starts with the crossing of two genotypes, such as an elite line of interest and one other elite inbred line having one or more desirable characteristics (i.e., having stably incorporated a polynucleotide of the invention, having a modulated activity and/or level of the polypeptide of the invention, etc) which complements the elite line of interest. If the two original parents do not provide all the desired characteristics, other sources can be included in the breeding population. In the pedigree method, superior plants are selfed and selected in successive filial generations. In the succeeding filial generations the heterozygous condition gives way to homogeneous lines as a result of self-pollination and selection. Typically in the pedigree method of breeding, five or more successive filial generations of selfing and selection is practiced: F1→F2; F2→F3; F3→F4; F4→F$_5$, etc. After a sufficient amount of inbreeding, successive filial generations will serve to increase seed of the developed inbred. In specific embodiments, the inbred line comprises homozygous alleles at about 95% or more of its loci.

In addition to being used to create a backcross conversion, backcrossing can also be used in combination with pedigree breeding to modify an elite line of interest and a hybrid that is made using the modified elite line. As discussed previously, backcrossing can be used to transfer one or more specifically desirable traits from one line, the donor parent, to an inbred called the recurrent parent, which has overall good agronomic characteristics yet lacks that desirable trait or traits. However, the same procedure can be used to move the progeny toward the genotype of the recurrent parent but at the same time retain many components of the non-recurrent parent by stopping the backcrossing at an early stage and proceeding with selfing and selection. For example, an F1, such as a commercial hybrid, is created. This commercial hybrid may be backcrossed to one of its parent lines to create a BC1 or BC2. Progeny are selfed and selected so that the newly developed inbred has many of the attributes of the recurrent parent and yet several of the desired attributes of the non-recurrent parent. This approach leverages the value and strengths of the recurrent parent for use in new hybrids and breeding.

Therefore, an embodiment of this invention is a method of making a backcross conversion of maize inbred line of interest, comprising the steps of crossing a plant of maize inbred line of interest with a donor plant comprising a mutant gene or transgene conferring a desired trait (i.e., increased pathogen resistance), selecting an F1 progeny plant comprising the mutant gene or transgene conferring the desired trait, and backcrossing the selected F1 progeny plant to the plant of maize inbred line of interest. This method may further comprise the step of obtaining a molecular marker profile of maize inbred line of interest and using the molecular marker profile to select for a progeny plant with the desired trait and the molecular marker profile of the inbred line of interest. In the same manner, this method may be used to produce an F1 hybrid seed by adding a final step of crossing the desired trait conversion of maize inbred line of interest with a different maize plant to make F1 hybrid maize seed comprising a mutant gene or transgene conferring the desired trait.

Recurrent selection is a method used in a plant breeding program to improve a population of plants. The method entails individual plants cross pollinating with each other to form progeny. The progeny are grown and the superior progeny selected by any number of selection methods, which include individual plant, half-sib progeny, full-sib progeny, selfed progeny and topcrossing. The selected progeny are cross-pollinated with each other to form progeny for another population. This population is planted and again superior plants are selected to cross pollinate with each other. Recurrent selection is a cyclical process and therefore can be repeated as many times as desired. The objective of recurrent selection is to improve the traits of a population. The improved population can then be used as a source of breeding material to obtain inbred lines to be used in hybrids or used as parents for a synthetic cultivar. A synthetic cultivar is the resultant progeny formed by the intercrossing of several selected inbreds.

Mass selection is a useful technique when used in conjunction with molecular marker enhanced selection. In mass selection seeds from individuals are selected based on phenotype and/or genotype. These selected seeds are then bulked and used to grow the next generation. Bulk selection requires growing a population of plants in a bulk plot, allowing the plants to self-pollinate, harvesting the seed in bulk and then using a sample of the seed harvested in bulk to plant the next generation. Instead of self pollination, directed pollination could be used as part of the breeding program.

Mutation breeding is one of many methods that could be used to introduce new traits into an elite line. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation; such as X-rays, Gamma rays (e.g. cobalt 60 or cesium 137), neutrons, (product of nuclear fission by uranium 235 in an atomic reactor), Beta radiation (emitted from radioisotopes such as phosphorus 32 or carbon 14), or ultraviolet radiation (preferably from 2500 to 2900 nm), or chemical mutagens (such as base analogues (5-bromo-uracil), related compounds (8-ethoxy caffeine), antibiotics (streptonigrin), alkylating agents (sulfur mustards, nitrogen mustards, epoxides, ethylenamines, sulfates, sulfonates, sulfones, lactones), azide, hydroxylamine, nitrous acid, or acridines. Once a desired trait is observed through mutagenesis the trait may then be incorporated into existing germplasm by traditional breeding techniques, such as backcrossing. Details of mutation breeding can be found in "Principles of Cultivar Development" Fehr, 1993 Macmillan Publishing Company the disclosure of which is incorporated herein by reference. In addition, mutations created in other lines may be used to produce a backcross conversion of elite lines that comprises such mutations.

As used herein, the term plant includes plant cells, plant protoplasts, plant cell tissue cultures from which maize plant can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides.

The present invention may be used to induce pathogen resistance or protect from pathogen attack any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereals*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal, and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Antipathogenic compositions, particularly antifungal compositions, are also encompassed by the present invention. Antipathogenic compositions may comprise antipathogenic polypeptides or transformed microorganisms comprising a nucleotide sequence that encodes an antipathogenic polypeptide, or antipathogenic domain thereof. The antipathogenic compositions of the invention may be applied to the environment of a plant pathogen, as described herein below, thereby protecting a plant from pathogen attack. Moreover, an antipathogenic composition can be formulated with an acceptable carrier that is, for example, a suspension, a solution, an emulsion, a dusting powder, a dispersible granule, a wettable powder, and an emulsifiable concentrate, an aerosol, an impregnated granule, an adjuvant, a coatable paste, and also encapsulations in, for example, polymer substances.

A gene encoding an antipathogenic, particularly antifungal, polypeptide of the invention may be introduced into any suitable microbial host according to standard methods in the art. For example, microorganism hosts that are known to occupy the "phytosphere" (phylloplane, phyllosphere, rhizosphere, and/or rhizoplane) of one or more crops of interest may be selected. These microorganisms are selected so as to be capable of successfully competing in the particular environment with the wild-type microorganisms, and to provide for stable maintenance and expression of the gene expressing the antifungal protein.

Such microorganisms include bacteria, algae, and fungi. Of particular interest are microorganisms such as bacteria, e.g., *Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc*, and *Alcaligenes*, fungi, particularly yeast, e.g., *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobacteria, Rhodopseudomonas spheroides, Xanthomonas campestris, Rhizobium melioti, Alcaligenes entrophus, Clavibacter xyli* and *Azotobacter vinlandir* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

Other illustrative prokaryotes, both Gram-negative and gram-positive, include *Enterobacteriaceae*, such as *Escherichia, Erwinia, Shigella, Salmonella*, and *Proteus; Bacillaceae; Rhizobiaceae*, such as *Rhizobium; Spirillaceae*, such as photobacterium, *Zymomonas, Serratia, Aeromonas, Vibrio, Desulfovibrio, Spirillum; Lactobacillaceae; Pseudomonadaceae*, such as *Pseudomonas* and *Acetobacter; Azotobacteraceae* and *Nitrobacteraceae*. Among eukaryotes are fungi, such as *Phycomycetes* and *Ascomycetes*, which includes yeast, such as *Saccharomyces* and *Schizosaccharomyces*; and *Basidiomycetes* yeast, such as *Rhodotorula, Aureobasidium, Sporobolomyces*, and the like.

Microbial host organisms of particular interest include yeast, such as *Rhodotorula* spp., *Aureobasidium* spp., *Saccharomyces* spp., and *Sporobolomyces* spp., phylloplane organisms such as *Pseudomonas* spp., *Erwinia* spp., and *Flavobacterium* spp., and other such organisms, including *Pseudomonas aeruginosa, Pseudomonas fluorescens, Sac-*

*charomyces cerevisiae, Bacillus thuringiensis, Escherichia coli, Bacillus subtilis*, and the like.

Genes encoding the antifungal proteins of the invention can be introduced into microorganisms that multiply on plants (epiphytes) to deliver antifungal proteins to potential target pests. Epiphytes, for example, can be gram-positive or gram-negative bacteria.

Root-colonizing bacteria, for example, can be isolated from the plant of interest by methods known in the art. Specifically, a *Bacillus cereus* strain that colonizes roots can be isolated from roots of a plant (see, for example, Handelsman et al. (1991) *Appl. Environ. Microbiol.* 56:713-718). Genes encoding the antifungal polypeptides of the invention can be introduced into a root-colonizing *Bacillus cereus* by standard methods known in the art.

Genes encoding antifungal proteins can be introduced, for example, into the root-colonizing *Bacillus* by means of electrotransformation. Specifically, genes encoding the antifungal proteins can be cloned into a shuttle vector, for example, pHT3101 (Lerecius et al. (1989) *FEMS Microbiol. Letts.* 60:211-218. The shuttle vector pHT3101 containing the coding sequence for the particular antifungal protein gene can, for example, be transformed into the root-colonizing Bacillus by means of electroporation (Lerecius et al. (1989) *FEMS Microbiol. Letts.* 60:211-218).

Methods are provided for protecting a plant from a pathogen comprising applying an effective amount of an antipathogenic protein or composition of the invention to the environment of the pathogen. "Effective amount" is intended to mean an amount of a protein or composition sufficient to control a pathogen. The antipathogenic proteins and compositions can be applied to the environment of the pathogen by methods known to those of ordinary skill in the art.

The antifungal compositions of the invention may be obtained by the addition of a surface-active agent, an inert carrier, a preservative, a humectant, a feeding stimulant, an attractant, an encapsulating agent, a binder, an emulsifier, a dye, a UV protective, a buffer, a flow agent or fertilizers, micronutrient donors, or other preparations that influence plant growth. One or more agrochemicals including, but not limited to, herbicides, insecticides, fungicides, bactericides, nematicides, molluscicides, acaricides, plant growth regulators, harvest aids, and fertilizers, can be combined with carriers, surfactants or adjuvants customarily employed in the art of formulation or other components to facilitate product handling and application for particular target pathogens. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention are normally applied in the form of compositions and can be applied to the crop area, plant, or seed to be treated. For example, the compositions of the present invention may be applied to grain in preparation for or during storage in a grain bin or silo, etc. The compositions of the present invention may be applied simultaneously or in succession with other compounds. Methods of applying an active ingredient of the present invention or an agrochemical composition of the present invention that contains at least one of the antipathogenic proteins, more particularly antifungal proteins, of the present invention include, but are not limited to, foliar application, seed coating, and soil application. The number of applications and the rate of application depend on the intensity of infestation by the corresponding pest or pathogen.

Suitable surface-active agents include, but are not limited to, anionic compounds such as a carboxylate of, for example, a metal; carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate or sodium cetyl sulfate; ethoxylated fatty alcohol sulfates; ethoxylated alkylphenol sulfates; lignin sulfonates; petroleum sulfonates; alkyl aryl sulfonates such as alkylbenzene sulfonates or lower alkylnaphtalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g., polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include but are not limited to inorganic minerals such as kaolin, phyllosilicates, carbonates, sulfates, phosphates, or botanical materials such as cork, powdered corncobs, peanut hulls, rice hulls, and walnut shells.

The antipathogenic compositions of the present invention can be in a suitable form for direct application or as a concentrate of primary composition that requires dilution with a suitable quantity of water or other diluent before application. The concentration of the antipathogenic polypeptide will vary depending upon the nature of the particular formulation, specifically, whether it is a concentrate or to be used directly. The composition contains 1 to 98% of a solid or liquid inert carrier, and 0 to 50%, optimally 0.1 to 50% of a surfactant. These compositions will be administered at the labeled rate for the commercial product, optimally about 0.01 lb-5.0 lb. per acre when in dry form and at about 0.01 pts.-10 pts. per acre when in liquid form.

In a further embodiment, the compositions, as well as the transformed microorganisms and antipathogenic proteins, of the invention can be treated prior to formulation to prolong the antipathogenic, particularly antifungal, activity when applied to the environment of a target pathogen as long as the pretreatment is not deleterious to the activity. Such treatment can be by chemical and/or physical means as long as the treatment does not deleteriously affect the properties of the composition(s). Examples of chemical reagents include but are not limited to halogenating agents; aldehydes such a formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) *Animal Tissue Techniques* (W. H. Freeman and Co.).

The antipathogenic compositions of the invention can be applied to the environment of a plant pathogen by, for example, spraying, atomizing, dusting, scattering, coating or pouring, introducing into or on the soil, introducing into irrigation water, by seed treatment or general application or dusting at the time when the pathogen has begun to appear or before the appearance of pathogens as a protective measure. For example, the antipathogenic protein and/or transformed microorganisms of the invention may be mixed with grain to protect the grain during storage. It is generally important to obtain good control of pathogens in the early stages of plant growth, as this is the time when the plant can be most severely damaged. The compositions of the invention can conveniently contain an insecticide if this is thought necessary. In one embodiment of the invention, the composition is applied directly to the soil, at a time of planting, in granular form of a composition of a carrier and dead cells of a *Bacillus* strain or transformed microorganism of the invention. Another embodiment is a granular form of a composition comprising an agrochemical such as, for example, a herbicide, an insecticide, a fertilizer, an inert carrier, and dead cells of a *Bacillus* strain or transformed microorganism of the invention.

Compositions of the invention find use in protecting plants, seeds, and plant products in a variety of ways. For example, the compositions can be used in a method that involves placing an effective amount of the antipathogenic, more particularly, antifungal, composition in the environment of the pathogen by a procedure selected from the group consisting of spraying, dusting, broadcasting, or seed coating.

Before plant propagation material (fruit, tuber, bulb, corm, grains, seed), but especially seed, is sold as a commercial product, it is customarily treated with a protective coating comprising herbicides, insecticides, fungicides, bactericides, nematicides, molluscicides, or mixtures of several of these preparations, if desired together with further carriers, surfactants, or application-promoting adjuvants customarily employed in the art of formulation to provide protection against damage caused by bacterial, fungal, or animal pests. In order to treat the seed, the protective coating may be applied to the seeds either by impregnating the tubers or grains with a liquid formulation or by coating them with a combined wet or dry formulation. In addition, in special cases, other methods of application to plants are possible, e.g., treatment directed at the buds or the fruit.

The plant seed of the invention comprising a DNA molecule comprising a nucleotide sequence encoding an antipathogenic polypeptide of the invention may be treated with a seed protective coating comprising a seed treatment compound, such as, for example, captan, carboxin, thiram, methalaxyl, pirimiphos-methyl, and others that are commonly used in seed treatment. Alternatively, a seed of the invention comprises a seed protective coating comprising an antipathogenic, more particularly antifungal, composition of the invention is used alone or in combination with one of the seed protective coatings customarily used in seed treatment.

The antifungal polypeptides of the invention can be used for any application including coating surfaces to target microbes. In this manner, the target microbes include human pathogens or microorganisms. Surfaces that might be coated with the antifungal polypeptides of the invention include carpets and sterile medical facilities. Polymer bound polypeptides of the invention may be used to coat surfaces. Methods for incorporating compositions with antimicrobial properties into polymers are known in the art. See U.S. Pat. No. 5,847,047, herein incorporated by reference.

The embodiments of the present invention may be effective against a variety of plant pathogens, particularly fungal pathogens, such as, for example, *Colletotrichum graminicola, Diplodia maydis, Fusarium graminearum*, and *Fusarium verticillioides*. Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Fungal pathogens, include but are not limited to, *Colletotrichum graminicola, Diplodia maydis, Fusarium graminearum*, and *Fusarium verticillioides*. Specific pathogens for the major crops include: Soybeans: *Phakopsora pachyrhizi, Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotrichum truncatum*), *Corynespora cassiicola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata*, Soybean mosaic virus, *Glomerella glycines*, Tobacco Ring spot virus, Tobacco Streak virus, *Phakopsora pachyrhizi, Pythium aphanidermatum, Pythium ultimum, Pythium debaryanum*, Tomato spotted wilt virus, *Heterodera glycines Fusarium solani*; Canola: *Albugo candida, Alternaria brassicae, Leptosphaeria maculans, Rhizoctonia solani, Sclerotinia sclerotiorum, Mycosphaerella brassicicola, Pythium ultimum, Peronospora parasitica, Fusarium roseum, Alternaria alternata*; Alfalfa: *Clavibacter michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium oxysporum, Verticillium albo-atrum, Xanthomonas campestris* p.v. *alfalfae, Aphanomyces euteiches, Stemphylium herbarum, Stemphylium alfalfae, Colletotrichum trifolii, Leptosphaerulina briosiana, Uromyces striatus, Sclerotinia trifoliorum, Stagonospora meliloti, Stemphylium botryosum, Leptotrichila medicaginis*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Colletotrichum graminicola, Erysiphe graminis* f.sp. *tritici, Puccinia graminis* f.sp. *tritici, Puccinia recondita* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomannes, Pythium ultimum, Bipolaris sorokiniana*, Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum*, High Plains Virus, European wheat striate virus; Sunflower: *Plasmopara halstedii, Sclerotinia sclerotiorum*, Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*; Corn: *Colletotrichum graminicola, Fusarium moniliforme* var. *subglutinans, Erwinia stewartii, F. verticillioides, Gibberella zeae*

(*Fusarium graminearum*), *Stenocarpella maydi* (*Diplodia maydis*), *Pythium irregulare*, *Pythium debaryanum*, *Pythium graminicola*, *Pythium splendens*, *Pythium ultimum*, *Pythium aphanidermatum*, *Aspergillus flavus*, *Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum*, *Physoderma maydis*, *Phyllosticta maydis*, *Kabatiella maydis*, *Cercospora sorghi*, *Ustilago maydis*, *Puccinia sorghi*, *Puccinia polysora*, *Macrophomina phaseolina*, *Penicillium oxalicum*, *Nigrospora oryzae*, *Cladosporium herbarum*, *Curvularia lunata*, *Curvularia inaequalis*, *Curvularia pallescens*, *Clavibacter michiganense* subsp. *nebraskense*, *Trichoderma viride*, Maize Dwarf Mosaic Virus A & B, Wheat Streak Mosaic Virus, Maize Chlorotic Dwarf Virus, *Claviceps sorghi*, *Pseudonomas avenae*, *Erwinia chrysanthemi* pv. *zea*, *Erwinia Carotovora*, Corn stunt *spiroplasma*, *Diplodia macrospora*, *Sclerophthora macrospora*, *Peronosclerospora sorghi*, *Peronosclerospora philippinensis*, *Peronosclerospora maydis*, *Peronosclerospora sacchari*, *Sphacelotheca reiliana*, *Physopella zeae*, *Cephalosporium maydis*, *Cephalosporium acremonium*, Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum*, *C. sublineolum*, *Cercospora sorghi*, *Gloeocercospora sorghi*, *Ascochyta sorghina*, *Pseudomonas syringae* p.v. *syringae*, *Xanthomonas campestris* p.v. *holcicola*, *Pseudomonas andropogonis*, *Puccinia purpurea*, *Macrophomina phaseolina*, *Perconia circinata*, *Fusarium moniliforme*, *Alternaria alternata*, *Bipolaris sorghicola*, *Helminthosporium sorghicola*, *Curvularia lunata*, *Phoma insidiosa*, *Pseudomonas avenae* (*Pseudomonas alboprecipitans*), *Ramulispora sorghi*, *Ramulispora sorghicola*, *Phyllachara sacchari*, *Sporisorium reilianum* (*Sphacelotheca reiliana*), *Sphacelotheca cruenta*, *Sporisorium sorghi*, Sugarcane mosaic H, Maize Dwarf Mosaic Virus A & B, *Claviceps sorghi*, *Rhizoctonia solani*, *Acremonium strictum*, *Sclerophthona macrospora*, *Peronosclerospora sorghi*, *Peronosclerospora philippinensis*, *Sclerospora graminicola*, *Fusarium graminearum*, *Fusarium oxysporum*, *Pythium arrhenomanes*, *Pythium graminicola*, etc.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

The article "a" and "an" are used herein to refer to one or more than one (i.e., to at least one) of the grammatical object of the article. By way of example, "an element" means one or more element.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The above-defined terms are more fully defined by reference to the specification as a whole.

The following examples are provided by way of illustration, not by way of limitation.

EXPERIMENTAL

Methods of growing fungal cultures are well known in the art. For subculturing the fungal cultures disclosed herein, any broth generally suitable for growing fungi may be used, including, for example, potato dextrose broth infra (Becton Dickinson Microbiology Systems, Sparks, Md.), Czapek-Dox broth infra (Becton Dickinson Microbiology Systems, Sparks Md.), Sabouraud broth (BBL #210986, Voigt Global Distribution LLC, Kansas City, Mo.), and the like.

Example 1

Isolation of Antifungal Polypeptide LB-12265
(SEQ ID NO:1)

An environmental sample was collected from the rhizosphere of the wildflower *Dianthus barbatus* L. (common name sweet William) in the Kiev region. The organism, denoted herein as IMV 00113, that produced the antifungal polypeptide SEQ ID NO: 1, was isolated using potato dextrose agar. The strain was later identified as *Fusarium oxysporum* Schlecht emend. Synd. et Hans. Molecular-level identification of the strain is still pending. The pure culture of the organism has been maintained at room temperature on malt extract agar slant by sub-culturing it in regular intervals. Isolate IMV 00113 was transferred to Berkeley Lab where the cultures were grown on PDA and preserved by placing 10 agar plugs per strain sampled with sterile P1000 plastic tips into 2 ml cryotubes containing 0.7 ml 45% (w/v) sterile glycerol. The cryotubes then were placed in a wooden block and frozen overnight in a −20° C. freezer at an approximate freezing rate of 1°/min. The now frozen material was transferred to a −84° C. freezer for long-term maintenance.

A designed set of specific growth conditions, i.e., nutrient content, temperature, pH, incubation time, aeration, etc., were applied to the isolated fungus to promote the production of secondary metabolites and novel natural products. The small molecule of interest was secreted by the above fungal strain when it was grown in 250-ml Erlenmeyer flasks filled with 50 ml of the following medium: maltose (12.75 g/l), malt extract (15 g/l), dextrin (2.75 g/l), glycerol (2.35 g/l), dibasic potassium phosphate (1 g/l), ammonium chloride (1 g/l), and bacto-peptone (0.75 g/l). The pH of the medium was adjusted with hydrochloric acid to a final value of 4.8 prior to autoclaving it at 15 psi for 15 min. The culture was incubated at 16° C. on an orbital shaker incubator at 180 rpm for 144 h. Biomass and supernatant were separated by centrifugation at 10,322×g, 15° C. for 20 min. Cell-free supernatant was frozen at −20° C. in 20-ml plastic scintillation vials. Samples were shipped overnight on dry ice.

The cell-free supernatant, designated LB-12265, of a large scale, 500-ml culture was provided and subjected to solid phase extraction, as described below.

Oasis HLB extraction cartridges (6 gram, 35 mL) (Waters Corporation, Milford, Mass.) were used for solid phase extraction (SPE). Specifically, the SPE cartridge was made wet with one cartridge volume of methanol and then conditioned with approximately 40 mL Solvent A (2% acetonitrile, 0.1% TFA). Approximately 90 milliliters of crude culture filtrate was treated with 5× solvent A to a final concentration of 1× and centrifuged for 20 min at 3,000×g. The supernatant was loaded onto an SPE cartridge, and the SPE cartridge was washed with approximately 40 mL solvent A. The SPE cartridge was eluted with approximately 40 mL 90% acetonitrile, 0.1% TFA. The eluted sample was partially dried in a centrifugal evaporator (Speed Vac) and frozen with liquid nitrogen and lyophilized to dryness.

The dried extract was re-suspended in phosphate buffered saline (PBS) (0.5 mL:20 mL starting culture filtrate), and the re-suspended extract was enriched for proteins using a Sephadex G10 (Amersham Biosciences AB, Uppsala, Sweden) spin column. Bio-Spin disposable chromatography columns (Bio-Rad Laboratories, Hercules CA) were filled to approximately 0.75 mL bed volume with Sephadex G10 that had been pre-equilibrated in phosphate buffered saline (PBS) and were centrifuged for 1 minute at 1,000×g. 200 µL of SPE extract in PBS was added to each pre-spun Bio-Spin column, and loaded Bio-Spin columns were centrifuged for 5 minutes at 1,000×g to elute proteins.

G10-treated antifungal extracts were fractionated by HPLC with a Jupiter 5µ C5 300 Å 150 mm×4.6 mm column (Phenomenex, Torrance, Calif.). HPLC starting conditions were 5% acetonitrile, 0.04% heptafluorobutyric acid (HFBA), 0.4 mL/minute. After injecting 200 µL of G10 treated antifungal extract, the flow rate was raised to 0.8 mL/minute over 1 minute. After an additional minute, a 94 minute exponentially curved gradient (Waters gradient curve 7, Waters Corporation, Milford, Mass.) was started to 86% acetonitrile, 0.04% HFBA. The HPLC fractions were divided into four ½ area 96 well clear bottom assay plates. Plates containing fractionated extracts were then dried in a centrifugal evaporator. The dried fractionated extracts were then screened for antifungal activity against FVE, CGR, FGR, and DMA using an antifungal plate assay, as described in Example 2. FVE, FGR and DMA were tested at 4,000 spores/mL in ¼× potato dextrose broth (Becton Dickinson Microbiology Systems, Sparks, Md.). CGR was tested at 4,000 spores/mL in ¼× Czapek-Dox (Becton Dickinson Microbiology Systems, Sparks Md.) +180 mL/L V8 juice. Cultures were allowed to develop at 27° C. for 24 hours. Assays were scored by visualizing fungal growth with an inverted microscope. The HPLC fractions from approximately 63 to 71.5 minutes were found to have antifungal activity against FVE, CGR, FGR and DMA.

Additional HPLC fractionations were performed to bulk up the antifungal fraction. This bulked up antifungal fraction was further purified using µ-bore HPLC with a Zorbax 3.5µ C8 300 Å 150 mm×1.0 mm column (Agilent Technologies, Palo Alto, Calif.). Starting conditions were 6.8% acetonitrile, 0.08% formic acid, 0.02% trifluoroacetic acid (TFA), 50 µL/minute. Two minutes following sample injection, a 33 minute linear gradient was started to 17.6% acetonitrile, 0.08% formic acid, 0.02% TFA. 214 nm peak based fractions were collected using an Agilent micro-fraction collector, dried in a centrifugal evaporator and assayed for antifungal activity as described above. A peak eluting at approximately 22.6 minutes was found to have broad-spectrum activity against FVE, CGR, FGR and DMA. ESI mass spectra were obtained on an integrated Agilent MSD TOF mass spectrometer.

Reduction and alkylation was required for efficient N-terminal sequencing. Approximately 10 µg of dried protein was re-suspended into 18 µL 0.1 M tricine, 8 M urea, pH 8.0. This solution was transferred to limited volume HPLC autosampler vial. 1 µL 200 mM DTT was added and the solution was incubated at 50° C. for 1 hour. Subsequently, 1 µL 500 mM 4-vinyl pyridine dissolved in acetonitrile was added, and the solution was incubated at 37° C. for 30 minutes in the dark. The iodoacetamide alkylation was then quenched by adding 20 µL 1% formic acid. The alkylated protein was purified by µ-bore HPLC on a Zorbax 3.5µ C8 300 Å 150 mm×1.0 mm column (Agilent Technologies, Palo Alto, Calif.). Starting conditions were 14% acetonitrile, 0.08% formic acid, 0.02% TFA. After 15 minutes a 45 minute linear gradient was performed to reach 54.5% acetonitrile, 0.08% formic acid, 0.02% TFA. The column flow rate was 50 µL/minute. 214 nm peak based fractions were collected using an Agilent micro fraction collector.

N-Terminal Sequencing

Initial N-terminal sequencing yielded the following sequence: SILHHCGKHASWDHAKSEC (SEQ ID NO:25). Further elucidation of the N-terminal sequence required sequencing of GluC digested fragments.

GluC Digestion

GluC (excision grade from *S. aureus*; Calbiochem cat. #324713) was prepared by adding water to achieve 0.5 µg/µL. ~5 µg 4-VP alkylated LB 12265 was suspended in 19.5 µL 25 mM ammonium carbonate pH 7.8 (pH adjusted with ammonium acetate). 0.5 µL GluC solution was added and mixed into 4-VP alkylated LB12265. The solution was incubated at 25° C. for 16 hours. Finally the solution was diluted with 20 µL 5% acetonitrile, 0.08% formic acid, 0.02% TFA, and injected onto a 1.0×150 mm Zorbax 300SB C8 3.5 µm column. Starting conditions were 5.9% acetonitrile, 0.08% formic acid, 0.02% trifluoroacetic acid (TFA) at a column flow rate of 50 µL/minute. Five minutes following sample injection, a 60 minute linear gradient was started to 23.9% acetonitrile, 0.08% formic acid, 0.02% TFA. 214 nm peak based fractions were collected using an Agilent micro-fraction collector. Masses for the isolated fragments were determined by splitting ~10% of the HPLC flow into an integrated Agilent MSD TOF mass spectrometer equipped with an ESI source. Seven peaks were collected, and sent for N-terminal sequencing.

N-Terminal Sequencing Results

```
Glu C digest peak F:
SILHHCGKHASWDHAKSE       (SEQ ID NO:26)

GluC Peak B:
SGKVYTKKHHKCKCPKGE       (SEQ ID NO:27)

Glu C Peak E:
KWHHIE                   (SEQ ID NO:28)

Glu C Peak D1:
SILHHCG                  (SEQ ID NO:29)

Glu C Peak D2:
SGKVYTK                  (SEQ ID NO:30)

GluC Peak V:
KKCKK                    (SEQ ID NO:31)
```

Example 2

Antifungal Activity of Polypeptide LB-12265 (SEQ ID NO:1)

The antifungal activity of the polypeptide of SEQ ID NO:1 against the fungal pathogens *Fusarium verticillioides* (FVE), *Colletotrichum graminicola* (CGR), *Fusarium graminearum* (FGR) and *Diplodia maydis* (DMA) was assessed using a standard plate assay.

Preparation of Cultures for Spore Production:

Cultures of FVE were prepared using V8 agar plates. FGR, CGR, and DMA cultures were prepared using ½× oatmeal agar. Media recipes are provided below.

Specifically, tubes containing silica-gel fungal stocks stored at −20° C. were briefly flamed, and approximately 5 crystals were sprinkled onto the agar surface. 2-3 plates of each fungal isolate were prepared. The newly plated cultures were stored in a plastic box to prevent the cultures from drying out. FVE cultures were grown in the dark at room temperature. CGR cultures were grown in ambient light at room temperature. FGR and DMA cultures were grown in an illuminated growth chamber at 27° C. New cultures were prepared every other week to maintain a consistent supply of spores.

Spore Preparation:

Spores were prepared from 2-4 week old cultures of FVE, FGR, CGR, and DMA. For FGR, FVE, and DMA, a portion of the culture plate was rinsed with a small amount of assay medium. The rinse solution was permitted to remain on the DMA plates for a time sufficient to allow the pycnidia rupture. The assay medium was then transferred to a sterile tube. Samples were vortexed, and spores were quantified using a hemacytometer.

For CGR, a sterile loop was gently dragged across orange areas of the culture plate. The loop was then inserted into a small volume of assay media, and the media was mixed with the loop to suspend the spores. Samples were vortexed, and spores were quantified using a hemacytometer.

Spores were diluted to the desired concentration with assay medium (4,000 spores per mL for FGR, FVE, and CGR, and 6,000 spores per mL for DMA) and kept on ice prior to beginning the antifungal activity assay.

Assay Plate Preparation Details:

Standard non-tissue culture treated 96 well flat bottom plates or ½ area non-treated plates (Costar) were used in the antifungal plate assays. Assay medium was ¼× potato dextrose broth for FVE, FGR and DMA, and ¼× Czapec-Dox V8 was used for CGR.

Antifungal polypeptides at various concentrations were added to the plates at 50 µL/well for a standard assay plate or 25 µL/well for a half area plate. An equal volume of media with fungal spores at 2 times the above concentrations was then added to start the assay. Alternatively HPLC fractionated lead samples were assayed by adding media with fungal spores (as above) into assay plates that the HPLC samples had been dried into (Savant Speed-vac). The plates were sealed with a gas permeable membrane ("Breathe-Easy", Cat. No. BEM-1, Diversified Biotech, Boston, Mass.), and the assay was allowed to develop in the dark at 28° C. for 24 to 48 hours.

After the incubation period, the plates were placed on an inverted microscope, and each well was examined and scored on a scale of 0-4, according to the following parameters: 0=no inhibition of fungal growth when compared to the negative control, 0.5=slight inhibition (overall growth is less than the negative control but growth from individual spores is not distinct), 1=slight inhibition (overall growth is less than the negative control but growth from individual spores is apparent, albeit not quite confluent), 2=moderate inhibition (growth from 1 spore can easily be identified and is significantly less abundant than the negative control; growth from each spore tends to look spherical), 3=strong inhibition (spores have germinated but growth is limited to a few branches of short hyphae), 4=complete inhibition (spores have not germinated. See, for example, Duvick et al. (1992) *J. Biol. Chem.* 267: 18814-18820). A score sheet containing representative examples of each level of antifungal activity is provided in FIG. 3.

Results

Figure 4:
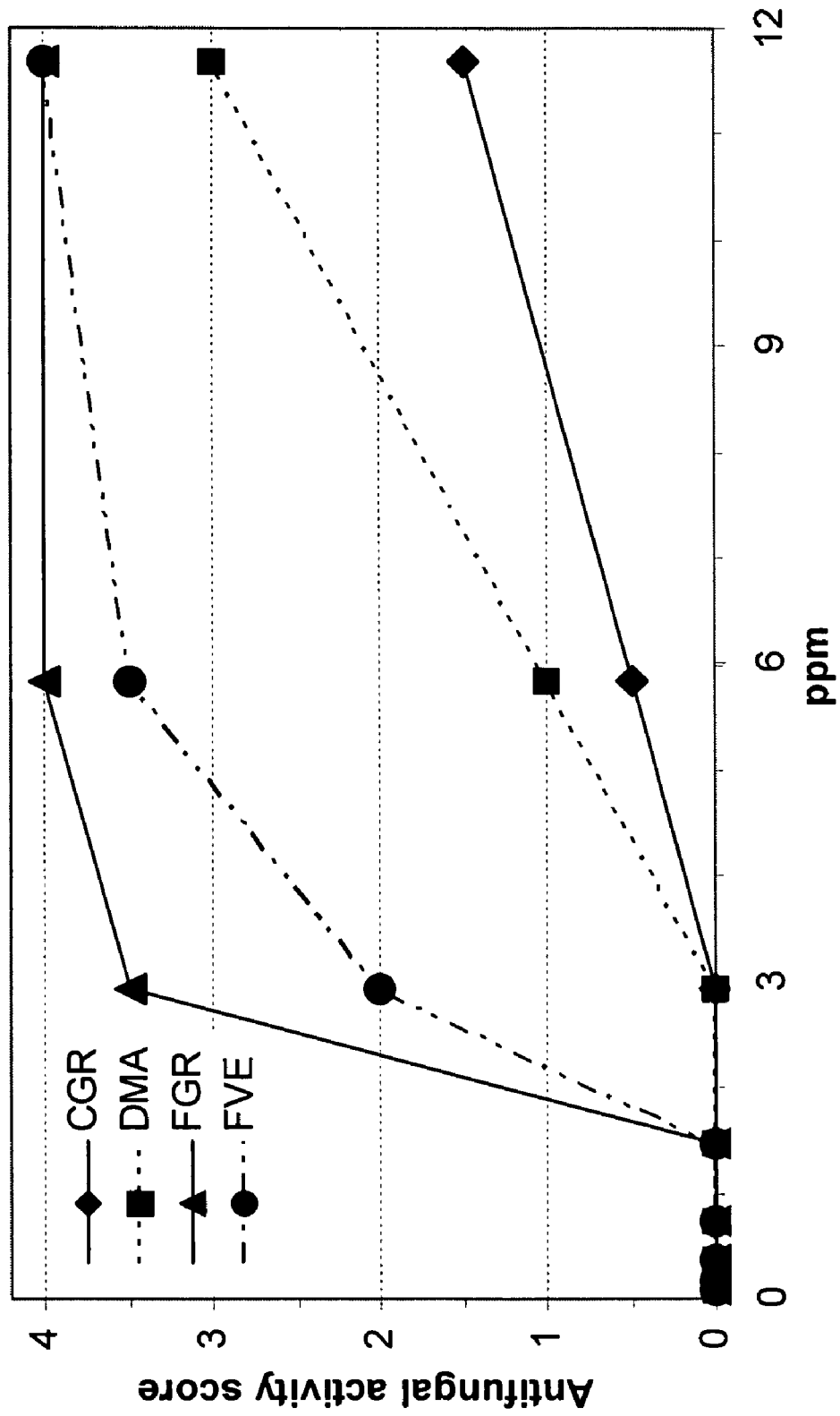
FIG. 4 provides the results of antifungal activity assays performed with the polypeptide set forth in SEQ ID NO:1, as described in Example 2. Antifungal activity against *Colletotrichum graminicola, Diplodia maydis, Fusarium graminearum*, and *Fusarium verticillioides* was observed.

FIG. 4 provides the results of antifungal activity assays with the polypeptide set forth in SEQ ID NO:1. This polypeptide showed antifungal activity against FVE, FGR, CGR, and DMA.

Media Recipes:

1× Czapek-Dox V8 Broth:

For each liter, suspend 35 grams Difco Czapek-Dox Broth (#233810) in dH$_2$O and add 180 milliliters V8 juice that has been clarified by centrifugation (3,000×g is plenty). Raise final volume to 1 liter and autoclave at 121° C. for 20 minutes. The media is filter sterilized to remove any remaining debris.

1× Potato Dextrose Broth:

For each liter, suspend 24 grams Difco Potato Dextrose Broth (#0549-17-9) in dH$_2$O and raise final volume to 1 liter and autoclave at 121° C. for 20 minutes. The media is filter sterilized to remove any remaining debris.

V8 Agar:

For each liter, dissolve 180 mL V8 juice and 3 grams calcium carbonate in 820 mL deionized water and then add 17 grams Bacto-agar in dH$_2$O in a 4 liter vessel. 10 drops of 5% antifoam A may be optionally added per liter prepared. Cover and autoclave at 121° C. for 20 minutes. Pour plates in sterile hood.

Oatmeal Agar:

For each liter, suspend 36.24 grams of Difco Oatmeal Agar (#0552-17-3) and 4.25 grams agar in dH$_2$O in a 4 liter vessel, cover and autoclave at 121° C. for 20 minutes. Pour plates in sterile hood.

| | FVE | FGR | CGR | DMA |
|---|---|---|---|---|
| Isolate name | MO33 | 73B ISU | Carroll-IA-99 | Warren-IN-96 |
| Medium for sporulation | V8 Agar | ½ × Oatmeal Agar | ½ × Oatmeal Agar | ½ × Oatmeal Agar |
| Agar culture age range for in vitro assay | 2-4 weeks old | 2-4 weeks old | 2-4 weeks old | 2-4 weeks old |
| Suggested schedule for starting agar cultures | Every other week | Every other week | Every other week | Every other week |
| Liquid medium for in vitro assay | ¼ × potato dextrose broth | ¼ × potato dextrose broth | ¼ × Czapec-Dox V8 broth | ¼ × potato dextrose broth |
| Spore Density for in vitro assay (spores/mL) | 4,000 | 4,000 | 4,000 | 6,000 |

Example 3

Isolation of Full-Length LB-12265 Gene from Genomic DNA

PCR was performed to isolate the full length LB-12265 gene from genomic DNA. The following materials were used in this process:

Materials Used

FastStart Taq DNA Polymerase Kit (Roche cat. #12032937001)

Hot Start Micro 50 Reaction Tubes (Molecular BioProducts cat. #6310)

PTC-100 Thermal Cycler from MJ Research, Inc dNTP's (Roche cat. #1277049)

Formamide (J.T. Baker cat. #4028-00)

Template and Primers

LB-12265 genomic DNA at a concentration of approximately 0.2 ug/μL was used as the template for the PCR reactions. Two primers were designed to the peptide sequence.

```
Sense Primer 93229
5'-CCATCAGGATCCGGCGGCCATGCTTCTCAACAA (SEQ ID NO:32)
GGCTTTCCTCGGC Anti-Sense Primer 93231
5'-CGTTGTGATATCTCACTTCTTGCACTTCTTCTC (SEQ ID NO:33)
AATGTGGTGCCACTTC
```

PCR

Lower and upper reaction mixtures were prepared as described below:
Lower: 36.3 μL dH2O, 5.5 μL of 10× (+MgCl2) PCR Buffer, 2.2 μL of Primer 93229 (from a 10 μM stock), 2.2 μL of Primer 93231 (from a 10 μM stock), and 8.8 μL of dNTP's (from a 2.5 mM stock)
Upper: 42.1 μL dH2O, 5.5 μL of 10×(+MgCl2) PCR Buffer, 3 μL of LB12265 template, 2.2 μL formamide, and 2.2 μL of Taq Polymerase (5 U/μL)

25 μL aliquots of lower mixture were placed into two Hot Start Tubes and were heated to 96° C. for one minute in the thermal cycler, which caused the wax inside to melt. The tubes were then cooled to 10° C. to harden the wax on top of the mixture. 25 μL aliquots of upper mixture were added to each Hot Start tube on top of the wax. PCR was performed using the following program on the thermal cycler:

| | | |
|---|---|---|
| 96° C. | 3 minutes | 1 cycle |
| 96° C. | 1 minute 5 seconds | 39 cycles |
| 55° C. | 1 minute 10 seconds | |
| 72° C. | 45 seconds | |
| 72° C. | 10 minutes | 1 cycle |
| 4° C. | | |

The PCR product was separated on a 2.5% low melt agarose gel and purified. The product was cut with BamHI and EcoRV, gel purified again, and then ligated into an Entry Vector for sequencing. The genomic sequence for LB-i12265 is set forth in SEQ ID NO:13 and encodes the predicted full-length polypeptide set forth in SEQ ID NO:14. The full-length LB-12265 polypeptide has a predicted signal peptide and propeptide region.

The cDNA encoding the full-length polypeptide sequence for cr1n.pk0189.g4 was similarly isolated as described above. The sequence is set forth in SEQ ID NO:23 and encodes the predicted full-length polypeptide set forth in SEQ ID NO:24. The full-length cr1n.pk0189.g4 polypeptide has a predicted signal peptide and propeptide region.

Example 4

Antifungal Activity of Polypeptides of SEQ ID NO:7, 9, and 11

The antifungal activity of the polypeptide of SEQ ID NO:1 against the fungal pathogens *Fusarium verticillioides* (FVE), *Colletotrichum graminicola* (CGR), *Fusarium graminearum* (FGR) and *Diplodia maydis* (DMA) was assessed using a standard plate assay, essentially as described in Example 2.

Results

FIG. 5A, B, and C provide the results of antifungal activity assays with the polypeptides set forth in SEQ ID NO:7, 9, and 11. All of these polypeptides showed antifungal activity to varying extents against FVE, FGR, CGR, and DMA.

Example 5

Antifungal Activity of Domains B, C, and D of SEQ ID NO:34

The antifungal activity of the B, C, and D domains of SEQ ID NO:34, which comprises the mature peptide of SEQ ID NO:9, against the fungal pathogen *Fusarium graminearum* (FGR) was assessed using a standard plate assay, essentially as described in Example 2.

Results

Figure 6:
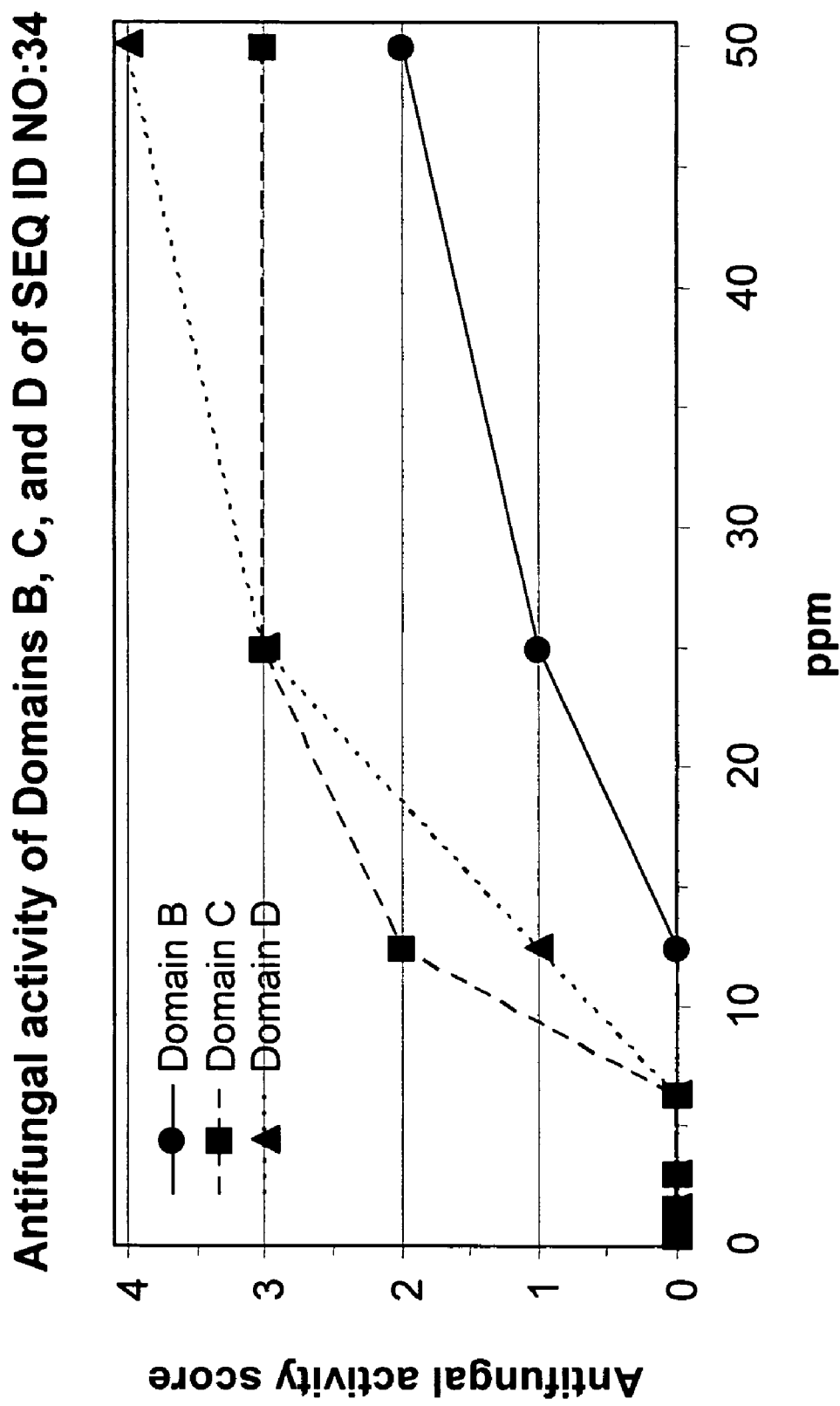
FIG. 6 provides the results of antifungal assays performed with the B, C, and D domains of the polypeptide set forth in SEQ ID NO:34, as described in Example 5. Antifungal activity against *Fusarium graminearum* was observed with all of the domains tested.

FIG. 6 provides the results of antifungal activity assays with the B, C, and D domains of SEQ ID NO:9 set forth in SEQ ID NOs:35-37. All of these polypeptides showed antifungal activity to varying extents against FGR.

Example 6

Transformation and Regeneration of Transgenic Maize Plants

Immature maize embryos from greenhouse donor plants are bombarded with a plasmid containing a nucleotide sequence encoding the antipathogenic polypeptide set forth in SEQ ID NO:1 operably linked to a promoter that drives expression in a maize plant cell and a selectable marker (e.g., the selectable marker gene PAT (Wohlleben et al. (1988) *Gene* 70:25-37), which confers resistance to the herbicide Bialaphos). Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising a nucleotide sequence encoding the antipathogenic polypeptide set forth in SEQ ID NO:1 operably linked to a promoter that drives expression in a maize cell is made. This plasmid DNA plus plasmid DNA containing a selectable marker (e.g., PAT) is precipitated onto 1.1 μm (average diameter) tungsten pellets using a CaCl$_2$ precipitation procedure as follows:

100 μL prepared tungsten particles in water
10 μL (1 μg) DNA in Tris EDTA buffer (1 μg total DNA)
100 μL 2.5 M CaCl$_2$
10 μL 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 mL 100% ethanol, and centrifuged for 30 seconds. Again the liquid is removed, and 105 μL 100% ethanol is added to the final tungsten particle pellet. For particle gun bombardment, the tungsten/DNA particles are briefly sonicated and 10 μL spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/L Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for fungal resistance.

Bombardment and Culture Media

Bombardment medium (560Y) comprises 4.0 g/L N6 basal salts (SIGMA C-1416), 1.0 mL/L Eriksson's Vitamin Mix (1000X SIGMA-1511), 0.5 mg/L thiamine HCl, 120.0 g/L sucrose, 1.0 mg/L 2,4-D, and 2.88 g/L L-proline (brought to volume with D-I $H_2O$ following adjustment to pH 5.8 with KOH); 2.0 g/L Gelrite (added after bringing to volume with D-I $H_2O$); and 8.5 mg/L silver nitrate (added after sterilizing the medium and cooling to room temperature). Selection medium (560R) comprises 4.0 g/L N6 basal salts (SIGMA C-1416), 1.0 mL/L Eriksson's Vitamin Mix (1000X SIGMA-1511), 0.5 mg/L thiamine HCl, 30.0 g/L sucrose, and 2.0 mg/L 2,4-D (brought to volume with D-I $H_2O$ following adjustment to pH 5.8 with KOH); 3.0 g/L Gelrite (added after bringing to volume with D-I $H_2O$); and 0.85 mg/L silver nitrate and 3.0 mg/L bialaphos (both added after sterilizing the medium and cooling to room temperature).

Plant regeneration medium (288J) comprises 4.3 g/L MS salts (GIBCO 11117-074), 5.0 mL/L MS vitamins stock solution (0.100 g nicotinic acid, 0.02 g/L thiamine HCL, 0.10 g/L pyridoxine HCL, and 0.40 g/L glycine brought to volume with polished D-I $H_2O$) (Murashige and Skoog (1962) Physiol. Plant. 15:473), 100 mg/L myo-inositol, 0.5 mg/L zeatin, 60 g/L sucrose, and 1.0 mL/L of 0.1 mM abscisic acid (brought to volume with polished D-I $H_2O$ after adjusting to pH 5.6); 3.0 g/L Gelrite (added after bringing to volume with D-I $H_2O$); and 1.0 mg/L indoleacetic acid and 3.0 mg/L bialaphos (added after sterilizing the medium and cooling to 60° C.). Hormone-free medium (272V) comprises 4.3 g/L MS salts (GIBCO 11117-074), 5.0 mL/L MS vitamins stock solution (0.100 g/L nicotinic acid, 0.02 g/L thiamine HCL, 0.10 g/L pyridoxine HCL, and 0.40 g/L glycine brought to volume with polished D-I $H_2O$), 0.1 g/L myo-inositol, and 40.0 g/L sucrose (brought to volume with polished D-I $H_2O$ after adjusting pH to 5.6); and 6 g/L bacto-agar (added after bringing to volume with polished D-I $H_2O$), sterilized and cooled to 60° C.

Example 7

Agrobacterium-mediated Transformation of Maize and Regeneration of Transgenic Plants For Agrobacterium-mediated transformation of maize with a nucleotide sequence encoding the polypeptide of SEQ ID NO:1, the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of Agrobacterium, where the bacteria are capable of transferring the polynucleotide construct to at least one cell of at least one of the immature embryos (step 1: the infection step). In this step the immature embryos are immersed in an Agrobacterium suspension for the initiation of inoculation. The embryos are co-cultured for a time with the Agrobacterium (step 2: the co-cultivation step). The immature embryos are cultured on solid medium following the infection step. Following this co-cultivation period an optional "resting" step is performed. In this resting step, the embryos are incubated in the presence of at least one antibiotic known to inhibit the growth of Agrobacterium without the addition of a selective agent for plant transformants (step 3: resting step). The immature embryos are cultured on solid medium with antibiotic, but without a selecting agent, for elimination of Agrobacterium and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

Example 8

Transformation of Somatic Soybean Embryo Cultures and Regeneration of Soybean Plants The following stock solutions and media are used for transformation and regeneration of soybean plants:

Stock Solutions
Sulfate 100 X Stock: 37.0 g $MgSO_4.7H_2O$, 1.69 g $MnSO_4.H_2O$, 0.86 g $ZnSO_4.7H_2O$, 0.0025 g $CuSO_4.5H_2O$.
Halides 100 X Stock: 30.0 g $CaCl_2.2H_2O$, 0.083 g KI, 0.0025 g $CoCl_2.6H_2O$,
P, B, Mo 100X Stock: 18.5 g $KH_2PO_4$, 0.62 g $H_3BO_3$, 0.025 g $Na_2MoO_4.2H_2O$
Fe EDTA 100X Stock: 3.724 g $Na_2EDTA$, 2.784 g $FeSO_4.7H_2O$.
2,4-D Stock: 10 mg/mL.
Vitamin B5 1000X Stock: 10.0 g myo-inositol, 0.10 g nicotinic acid, 0.10 g pyridoxine HCl, 1 g thiamine.

Media (Per Liter)
SB196: 10 mL of each of the above stock solutions, 1 mL B5 vitamin stock, 0.463 g $(NH_4)_2 SO_4$, 2.83 g $KNO_3$, 1 mL 2,4-D stock, 1 g asparagine, 10 g sucrose, pH 5.7.

SB103: 1 pk. Murashige & Skoog salts mixture, 1 mL B5 vitamin stock, 750 mg MgCl₂ hexahydrate, 60 g maltose, 2 g gelrite, pH 5.7.

SB166: SB103 supplemented with 5 g per liter activated charcoal.

SB71-4: Gamborg's B5 salts (Gibco-BRL catalog No. 21153-028), 1 mL B5 vitamin stock, 30 g sucrose, 5 g TC agar, pH 5.7.

Soybean embryogenic suspension cultures are maintained in 35 mL liquid medium (SB196) on a rotary shaker (150 rpm) at 28° C. with fluorescent lights providing a 16 hour day/8 hour night cycle. Cultures are subcultured every 2 weeks by inoculating approximately 35 mg of tissue into 35 mL of fresh liquid media.

Soybean embryogenic suspension cultures are transformed by the method of particle gun bombardment (see Klein et al. (1987) *Nature* 327:70-73) using a DuPont Biolistic PDS1000/He instrument.

In particle gun bombardment procedures it is possible to use purified 1) entire plasmid DNA or, 2) DNA fragments containing only the recombinant DNA expression cassette(s) of interest. For every eight bombardment transformations, 30 μl of suspension is prepared containing 1 to 90 picograms (pg) of DNA fragment per base pair of DNA fragment. The recombinant DNA plasmid or fragment used to express the antifungal gene is on a separate recombinant DNA plasmid or fragment from the selectable marker gene. Both recombinant DNA plasmids or fragments are co-precipitated onto gold particles as follows. The DNAs in suspension are added to 50 μL of a 20-60 mg/mL 0.6 μm gold particle suspension and then combined with 50 μL CaCl₂ (2.5 M) and 20 μL spermidine (0.1 M) The mixture is pulse vortexed 5 times, spun in a microfuge for 10 seconds, and the supernatant removed. The DNA-coated particles are then washed once with 150 μL of 100% ethanol, pulse vortexed and spun in a microfuge again, and resuspended in 85 μL of anhydrous ethanol. Five μL of the DNA-coated gold particles are then loaded on each macrocarrier disk.

Approximately 150 to 250 mg of two-week-old suspension culture is placed in an empty 60 mm×15 mm petri plate and the residual liquid is removed from the tissue using a pipette. The tissue is placed about 3.5 inches away from the retaining screen and each plate of tissue is bombarded once. Membrane rupture pressure is set at 650 psi and the chamber is evacuated to −28 inches of Hg. Eighteen plates are bombarded, and, following bombardment, the tissue from each plate is divided between two flasks, placed back into liquid media, and cultured as described above.

Seven days after bombardment, the liquid medium is exchanged with fresh SB196 medium supplemented with 50 mg/mL hygromycin or 100 ng/mL chlorsulfuron, depending on the selectable marker gene used in transformation. The selective medium is refreshed weekly or biweekly. Seven weeks post-bombardment, green, transformed tissue is observed growing from untransformed, necrotic embryogenic clusters. Isolated green tissue is removed and inoculated into individual flasks to generate new, clonally-propagated, transformed embryogenic suspension cultures. Thus, each new line is treated as independent transformation event. These suspensions can then be maintained as suspensions of embryos clustered in an immature developmental stage through subculture or can be regenerated into whole plants by maturation and germination of individual somatic embryos.

Transformed embryogenic clusters are removed from liquid culture and placed on solid agar medium (SB 166) containing no hormones or antibiotics for one week. Embryos are cultured at 26° C. with mixed fluorescent and incandescent lights on a 16 hour day:8 hour night schedule. After one week, the cultures are then transferred to SB 103 medium and maintained in the same growth conditions for 3 additional weeks. Prior to transfer from liquid culture to solid medium, tissue from selected lines is assayed by PCR or Southern analysis for the presence of the antifungal gene.

Somatic embryos become suitable for germination after 4 weeks and are then removed from the maturation medium and dried in empty petri dishes for 1 to 5 days. The dried embryos are then planted in SB71-4 medium where they are allowed to germinate under the same light and germination conditions described above. Germinated embryos are transferred to sterile soil and grown to maturity.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purpose of clarity of understanding, it will be obvious that certain changes and modifications may be practiced within the scope of the appended claims.

That which is claimed:

1. An antipathogenic composition comprising a carrier and at least one polypeptide selected from the group consisting of:
   a) a polypeptide comprising the amino acid sequence set forth in SEQ ID NO:1 or 5; and
   b) a polypeptide having at least 95% sequence identity to SEQ ID NO:1 or 5; wherein said polypeptide has antipathogenic activity.

2. A method for protecting a plant from a plant fungal pathogen comprising applying the composition according to claim 1 to the environment of a plant fungal pathogen.

3. The method of claim 2, wherein said composition is applied by a procedure selected from the group consisting of spraying, dusting, broadcasting, and seed coating.

* * * * *

SEQUENCE LISTING

<160> NUMBER OF SEQ ID NOS: 37

<210> SEQ ID NO 1
<211> LENGTH: 52
<212> TYPE: PRT
<213> ORGANISM: Fusarium oxysporum
<220> FEATURE:
<221> NAME/KEY: PEPTIDE
<222> LOCATION: (1)...(52)
<223> OTHER INFORMATION: Predicted mature LB-12265 peptide

<400> SEQUENCE: 1

Ser Ile Leu His His Cys Gly Lys His Ala Ser Trp Asp His Ala Lys
1               5                   10                  15

Ser Glu Cys Val Cys His Asp Ser Gly Lys Val Tyr Thr Lys Lys His
            20                  25                  30

His Lys Cys Lys Cys Pro Lys Gly Glu Lys Trp His His Ile Glu Lys
         35                  40                  45

Lys Cys Lys Lys
    50

<210> SEQ ID NO 2
<211> LENGTH: 156
<212> TYPE: DNA
<213> ORGANISM: Fusarium oxysporum
<220> FEATURE:
<221> NAME/KEY: mat_peptide
<222> LOCATION: (1)...(156)
<223> OTHER INFORMATION: Nucleotide sequence encoding the predicted
      mature LB-12265 peptide

<400> SEQUENCE: 2
agcatccttc accactgcgg caagcacgct tcttgggatc acgccaagag cgagtgcgtg      60
tgccacgact ccggcaaggt ctacaccaag aagcaccaca agtgcaagtg ccccaagggc     120
gagaagtggc accacattga aagaagtgc aagaag                                156

<210> SEQ ID NO 3
<211> LENGTH: 52
<212> TYPE: PRT
<213> ORGANISM: Unknown
<220> FEATURE:
<223> OTHER INFORMATION: Deduced amino acid sequence encoded by SEQ ID
      NO:4 from a fungal contaminant of Zea mays
<220> FEATURE:
<221> NAME/KEY: PEPTIDE
<222> LOCATION: (1)...(52)
<223> OTHER INFORMATION: Predicted mature cr1n.pk0189.g4 peptide

<400> SEQUENCE: 3

Ser Ile Leu His His Cys Gly Lys His Ala Ser Trp Asp His Ala Lys
 1               5                  10                  15

Ser Glu Cys Val Cys His Asp Ser Gly Lys Val Tyr Thr Lys Lys His
             20                  25                  30

His Lys Cys Lys Cys Pro Lys Gly Glu Lys Trp His His Ile Glu Lys
         35                  40                  45

Lys Cys Lys Lys
    50

<210> SEQ ID NO 4
<211> LENGTH: 156
<212> TYPE: DNA
<213> ORGANISM: Unknown
<220> FEATURE:
<223> OTHER INFORMATION: Nucletoide sequence isolated from a fungal
      contaminant of Zea mays
<220> FEATURE:
<221> NAME/KEY: mat_peptide
<222> LOCATION: (1)...(156)
<223> OTHER INFORMATION: Nucleotide sequence encoding the predicted
      mature cr1n.pk0189.g4 peptide

<400> SEQUENCE: 4
agcatccttc accactgtgg caagcacgct tcctgggatc acgccaagag cgagtgcgta      60
tgccacgact ccggcaaggt ctacaccaag aagcaccaca agtgcaagtg ccccaagggc     120
gagaagtggc accacattga aagaagtgc aagaag                                156

<210> SEQ ID NO 5
<211> LENGTH: 85
<212> TYPE: PRT
<213> ORGANISM: Artificial Sequence
<220> FEATURE:
<223> OTHER INFORMATION: Deduced amino acid sequence encoded by SEQ ID
      NO:6 from a Fusarium verticillioides subtraction library

<400> SEQUENCE: 5

Met Leu Leu Asn Lys Ala Phe Leu Gly Ala Leu Leu Ala Met Gly Thr
1               5                   10                  15

Val Thr Ala Leu Pro Asn Pro Asp Ala Glu Pro Val Asp Leu Glu Asp
            20                  25                  30

Arg Ser Ile Leu His His Cys Gly Lys His Ala Ser Trp Asp His Ala
        35                  40                  45

Lys Ser Glu Cys Val Cys His Asp Ser Gly Lys Val Tyr Thr Lys Lys
    50                  55                  60

His His Lys Cys Lys Cys Pro Lys Gly Glu Lys Trp His His Ile Glu
65                  70                  75                  80

Lys Lys Cys Lys Lys
                85

<210> SEQ ID NO 6
<211> LENGTH: 415
<212> TYPE: DNA
<213> ORGANISM: Fusarium verticillioides
<220> FEATURE:
<221> NAME/KEY: variation
<222> LOCATION: 397
<223> OTHER INFORMATION: n = any nucleotide

<400> SEQUENCE: 6
tactcaagcc cataacccag ttgtcggccc agagatgtaa atctttcgag tatatagaac      60
tctttgcgat ggatgtcgag gttgacttgt tgtgatcgta gggacgtcta gtgcagacgc     120
ttatttcttg cacttcttct caatgtggtg ccacttctcg cccttggggc acttgcactt     180
gtggtgcttc ttggtgtaga ccttgccgga gtcgtggcat acacactcgc tcttggcgtg     240
atcccaggaa gcgtgtttgc cgcagtggtg aaggatgctg cgatcctcga gatcaacggg     300
ctcagcgtcg gggttgggga gggcggtgac tgtgcccatg gcgaggaggg cgccgaggaa     360
agccttgttg agaagcatga tgaaggtatg agttggntag ttgagtttgt gacct          415

<210> SEQ ID NO 7
<211> LENGTH: 279
<212> TYPE: PRT
<213> ORGANISM: Artificial Sequence
<220> FEATURE:
<223> OTHER INFORMATION: Deduced amino acid sequence encoded by SEQ ID
      NO:8 from a Fusarium sporotrichioides cDNA library

<400> SEQUENCE: 7

Met Leu Phe Asn Lys Leu Phe Leu Gly Ala Ile Leu Ala Met Thr Ser
1               5                   10                  15

Val Ala Ala Ile Pro Asn Pro Val Ala Glu Pro Gly Ser Leu Val Glu
            20                  25                  30

Arg Ser Lys His His Asp His His Asp Cys Gly Lys His Ala Ser Tyr
        35                  40                  45

Asn Glu Glu Lys Lys Glu Cys Val Cys His Ala Ser Gly Glu Thr Tyr
    50                  55                  60

His Lys Lys His Lys Lys Cys Lys Lys Glu Lys Glu Asp Lys Lys His
65                  70                  75                  80

Lys Thr Glu Arg Asp Ile Ile Ala Glu Arg Ser Pro Lys Lys His Lys
                85                  90                  95

```
Asp Ser His His Cys Gly Lys His Ala Ser Tyr Asn Glu Glu Lys Met
            100                 105                 110

Glu Cys Val Cys His Asp Ser Ser Glu Val Phe Glu Lys His His Lys
        115                 120                 125

Lys Cys Lys Lys Ser Lys Asp Val Lys Lys Val Asp Asp Lys Lys
    130                 135                 140

Lys Ala Lys Asp Asp Lys Lys Ser Asn Asp Lys Lys Ser Asp Asp
145                 150                 155                 160

Lys Lys Ser Lys Asp Gly Lys Gly Pro Lys Ser Glu Arg Asp Val Ile
                165                 170                 175

Ala Glu Arg Ser Pro Lys Lys His Lys Asp His Asp Arg Cys Gly Lys
            180                 185                 190

His Ala Ser Tyr Ser Glu Glu Lys Lys Glu Cys Val Cys His Asn Lys
        195                 200                 205

Ala Glu Ile Phe Glu Arg Lys His Lys Cys Lys Lys His Ile Ser
    210                 215                 220

Leu Arg Ser Ile Leu His His Cys Gly Arg Glu Ala Tyr Tyr Asp Asp
225                 230                 235                 240

Ala Lys Asn Glu Cys Ile Cys His Asp Ser Gly Lys Asp Phe Leu Lys
                245                 250                 255

Lys His Lys Thr Cys Ala Cys Pro Gln Gly Glu Lys Trp His His Ile
            260                 265                 270

Glu Arg Lys Cys Ser Arg His
        275

<210> SEQ ID NO 8
<211> LENGTH: 467
<212> TYPE: DNA
<213> ORGANISM: Fusarium sporotrichioides

<400> SEQUENCE: 8
atatacacga acctgctcga caagccttaa tcatgctctt caacaaactg tttcttggcg      60
ctatcctcgc catgacctct gtggctgcca ttcccaaccc tgttgctgag cctggaagtc     120
ttgtggagcg cagtaagcac cacgaccatc atgactgtgg caagcatgct tcctataatg     180
aggaaaagaa ggaatgtgtt tgccatgcca gcggggagac ctaccacaag aagcataaga     240
agtgcaagaa agaaaaggaa gacaagaagc acaagacaga gcgagacatt atcgcagagc     300
gcagccccaa gaagcacaag gactctcacc actgtggaaa gcatgcttct tacaacgaag     360
aaaagatgga gtgtgtctgt cacgacagct ccgaggtctt cgagaagcac acaaaaagt     420
gcaagaagtc caaggacgtc aagaaggtag tggatgacaa gaagaag                   467

<210> SEQ ID NO 9
<211> LENGTH: 248
<212> TYPE: PRT
<213> ORGANISM: Gibberella zeae

<400> SEQUENCE: 9

Met Arg Phe Ser Asn Leu Phe Leu Gly Ala Val Phe Ala Val Thr Ser
 1               5                  10                  15

Val Ala Ala Met Ala Asn Pro Ala Ala Glu Ala Gly Ser Leu Met Glu
            20                  25                  30

Arg Ser Lys His His His Asp Cys Gly Lys His Ala Ser Tyr Asn Thr
        35                  40                  45

Glu Lys Lys Glu Cys Val Cys His Val Ser Gly Glu Thr Tyr His Lys
    50                  55                  60
```

```
Lys His His Lys Cys Lys Pro Lys Glu Asp Lys Lys His His Ser
 65                  70                  75                  80

Arg Asp Val Leu Glu Glu Arg Ser Pro Lys Lys Asp Glu His Glu His
                 85                  90                  95

Cys Gly Lys His Ala Ser Phe Asn Glu Glu Lys Lys Glu Cys Val Cys
            100                 105                 110

His Asp Lys Ser Glu Val Phe Glu Lys His His Lys Lys Cys Lys Lys
        115                 120                 125

Ala Lys Asp Glu Lys Lys Lys Asp Asp Lys Lys His His Ser Arg Asp
    130                 135                 140

Val Leu Glu Glu Arg Asp Pro Lys Lys Asp Lys His His Asp His Cys
145                 150                 155                 160

Gly Lys His Ala Ser Tyr Ser Glu Glu Lys Lys Glu Cys Val Cys His
                165                 170                 175

Asn Lys Ala Glu Val Phe Glu Arg Lys His Lys Lys Cys Lys Lys His
            180                 185                 190

Ile Ser Leu Arg Ser Ile Phe Asn His Cys Gly Arg His Ala Tyr Tyr
        195                 200                 205

Asp Glu Ala Lys Lys Glu Cys Ile Cys His Asp Ala Gly Lys Asp Phe
    210                 215                 220

Leu Lys Lys His Lys Thr Cys Ala Cys Pro Gln Gly Glu Lys Trp His
225                 230                 235                 240

His Ile Glu Arg Lys Cys Lys Ala
                245

<210> SEQ ID NO 10
<211> LENGTH: 747
<212> TYPE: DNA
<213> ORGANISM: Gibberella zeae

<400> SEQUENCE: 10
atgcggttca gcaaccttt  ccttggcgct gtcttcgccg tgacttcggt cgctgccatg      60
gccaaccctg ccgccgaggc cggaagtctt atggagcgca gcaagcatca ccatgactgc     120
ggcaaacatg cctcctacaa caccgagaag aaggaatgtg tctgccatgt cagcggcgag     180
acctaccaca gaagcaccca agtgcaag   aagcctaagg aagacaagaa gcaccactca     240
agagacgttc ttgaggagcg cagccccaag aaggacgagc acgaacactg cggcaagcac     300
gcttccttca cgaagagaa  gaaggagtgt gtctgccacg ataagtccga gttttttgag     360
aagcaccaca gaagtgcaa  gaaggcaaag gatgagaaga agaaggacga caagaagcac     420
cactcacgag atgtcctcga ggaacgtgac cccaagaagg ataagcacca cgaccactgc     480
ggcaagcacg cctcttacag cgaggagaag aaggaatgcg tctgccacaa caaagccgag     540
gtctttgaaa ggaagcacaa gaagtgcaag aagcacatct ctctgcgaag catcttcaac     600
cactgcggcc gacatgctta ctacgatgag gccaagaagg agtgcatctg ccacgacgcc     660
ggcaaggact tcctcaagaa gcacaagacc tgcgcttgcc ctcagggtga gaagtggcac     720
cacattgagc gcaagtgcaa ggcttaa                                          747

<210> SEQ ID NO 11
<211> LENGTH: 704
<212> TYPE: PRT
<213> ORGANISM: Hypocrea lixii
```

-continued

<400> SEQUENCE: 11

```
Met Leu Leu Lys Gln Val Leu Val Ala Ala Leu Leu Ser Leu Ser Ser
1               5                   10                  15

Val Thr Ala Phe Pro Asn Pro Asn Asn Leu His Asp Val Glu Ala Arg
            20                  25                  30

Asp Val Glu Asp Asn Leu Val Ala Arg Gly Gly Ser His Asp Cys Gly
        35                  40                  45

Ser Tyr Ala Ser Trp Asn Asn Gly Lys Asn Cys Cys Val Cys Lys Asp
    50                  55                  60

Asn Gly Lys Asn Tyr Asp Ser Lys Ser Lys Ser Cys Asn Cys Pro Ser
65                  70                  75                  80

Gly Tyr Thr Trp Asn Gly His Gln Cys Val His Asp Cys Gly Lys Asp
                85                  90                  95

Ala Thr Trp Gln Tyr Gly Asn Cys Val Cys Asn Lys Lys Gly Glu Val
            100                 105                 110

Tyr Asn Pro Lys Asp Lys Thr Cys Ser Cys Pro Pro Gly Gln Tyr Trp
        115                 120                 125

Asn Gly Lys Asn Cys Gln Val Asp Cys Gly Lys Asp Ala Ser Tyr Asp
    130                 135                 140

Tyr Lys Gln Lys Lys Cys Val Cys Lys Lys His Gly Glu Ile Tyr Asn
145                 150                 155                 160

Ser Asn Ser Lys Thr Cys Ser Cys Pro Pro Gly Gln Val Trp Asn Gly
                165                 170                 175

Tyr Ala Cys Val Val Asp Cys Gly Lys Glu Ala His Phe Asp Asn Lys
            180                 185                 190

Gln Lys Lys Cys Val Cys Asn Asn Tyr Gly Glu Ile Tyr Asn Ser Gly
        195                 200                 205

Ser Lys Thr Cys Ala Cys Pro Gly Gly Gln Tyr Phe Asn Gly Lys Lys
    210                 215                 220

Cys Val Cys Pro Tyr Gly Lys Val Trp Asn Gly Lys Gln Cys Val Glu
225                 230                 235                 240

Asp Cys Gly Lys Glu Ala His Phe Asp Tyr Asn Gln Lys Lys Cys Val
                245                 250                 255

Cys Lys Asn Asn Gly Glu Val Tyr Asn Ser Ala Lys Lys Thr Cys Ser
            260                 265                 270

Cys Pro Asp Gly Gln Tyr Trp Asn Gly Lys Gln Cys Val Cys Pro Tyr
        275                 280                 285

Gly Gln Val Phe Asn Gly Lys Gln Cys Val Pro Asp Cys Gly Lys Glu
    290                 295                 300

Ala Thr Phe Asp Tyr Asn Gln Lys Lys Cys Val Cys Lys Asn Lys Gly
305                 310                 315                 320

Glu Ile Tyr Asp Ser Lys Thr Lys Thr Cys Ser Cys Pro Asp Gly Gln
                325                 330                 335

Val Trp Asn Gly Lys Gln Cys Val Cys Pro Tyr Gly Gln Val Phe Asn
            340                 345                 350

Gly Lys Gln Cys Val Pro Asp Cys Gly Lys Asp Ala Thr Tyr Asp Tyr
        355                 360                 365

Asn Gln Lys Lys Cys Val Cys Lys Asn Lys Gly Glu Val Phe Asp Gln
    370                 375                 380

Lys Thr Lys Thr Cys Ser Cys Pro Asp Gly Gln Tyr Trp Asn Gly Lys
385                 390                 395                 400

Gln Cys Ala Cys Pro Tyr Gly Gln Ile Phe Asn Gly Lys Gln Cys Val
                405                 410                 415
```

```
Pro Asp Cys Gly Lys Asp Ala Thr Tyr Asp Tyr Asn Gln Lys Lys Cys
            420                 425                 430

Val Cys Lys Asn Lys Gly Glu Val Phe Asp Gln Lys Thr Lys Thr Cys
            435                 440                 445

Ser Cys Pro Asp Gly Gln Tyr Trp Asn Gly Lys Gln Cys Val Cys Pro
            450                 455                 460

Tyr Gly Lys Ile Phe Asp Gly Lys Gln Cys Val Glu Asp Cys Gly Lys
465                 470                 475                 480

Asp Ala His Phe Asp Asn Asn Gln Lys Lys Cys Val Cys Asn Lys Asn
                485                 490                 495

Gly Glu Ile Tyr Asp Ser Lys Ser Lys Thr Cys Ser Cys Pro Asp Ser
            500                 505                 510

Gln Tyr Trp Asp Gly Ser Lys Cys Ala Cys Pro Tyr Gly Thr Val Trp
            515                 520                 525

Asp Gly Lys His Cys Asn Gln Asp Cys Gly Lys Asp Ala His Phe Asp
            530                 535                 540

Ser Asn Gln Lys Lys Cys Val Cys Asn Lys Gln Gly Glu Val Tyr Asp
545                 550                 555                 560

Ser Lys Ser Lys Thr Cys Ser Cys Pro Asp Gly Gln Tyr Trp Asp Gly
                565                 570                 575

Ser Lys Cys Ala Cys Pro Tyr Gly Lys Val Trp Asp Gly Lys Gln Cys
            580                 585                 590

Val Pro Asn Cys Gly Lys Asp Ala Ser Tyr Asp Ser Lys Gln Asn Lys
            595                 600                 605

Cys Val Cys Lys Asn Ile Gly Gln Val Phe Asp Thr Lys Ser Leu Thr
            610                 615                 620

Cys Ser Cys Pro Ala Gly Thr Ser Trp Asn Gly His Ala Cys Val Gln
625                 630                 635                 640

Asp Cys Gly Lys Asp Ala His Tyr Asp Ser Asn Gln Lys Cys Cys Val
                645                 650                 655

Cys Asn Asn Lys Gly Glu Ser Tyr Asp Ser Lys Ser Lys Thr Cys Ser
            660                 665                 670

Cys Pro Gly Asn Gln Tyr Trp Asp Gly Asn Lys Cys Ala Cys Pro Tyr
            675                 680                 685

Gly Ser Thr Trp Asp Ser Ser Lys Lys Thr Cys Lys Met Asn Tyr Pro
690                 695                 700

<210> SEQ ID NO 12
<211> LENGTH: 2115
<212> TYPE: DNA
<213> ORGANISM: Hypocrea lixii

<400> SEQUENCE: 12
atgttgctta agcaggtcct tgtggccgct ctgctctctt tgagctctgt cacggctttc      60
ccaaacccga caacctcca  tgacgtggag gctaggatg  tcgaagacaa cctcgttgcc     120
cgtggcggtt cccacgactg tggctcttat gccagctgga caacggaaa  gaactgctgt     180
gtctgcaaag acaatggcaa gaactacgat tccaagtcaa agtcatgcaa ctgccccagt     240
ggctacacct ggaatggtca ccagtgcgtc cacgactgtg caaagacgc  tacttggcag     300
tatggaaact gtgtctgcaa caagaaaggc gaagtctaca ccccaagga  caagacctgc     360
agctgcccac aggacaata  ctggaacggc aagaactgcc aggtcgattg cggcaaagac     420
gcttcatatg actacaagca gaagaaatgc gtttgcaaga aacacggcga atctacaac     480
tccaactcca agacttgcag ctgccccct  ggccaggttt ggaacggcta cgcatgcgtt     540
```

```
gttgactgtg gcaaggaagc gcactttgac aataaacaga agaagtgtgt gtgcaacaac       600
tacggcgaaa tctacaactc tggcagcaaa acttgcgctt gccctggagg acaatacttc       660
aacggcaaga aatgcgtttg cccgtacggt aaagtctgga acggtaaaca gtgtgtagaa       720
gactgcggca aggaagccca cttcgactat aaccagaaga agtgtgtgtg caaaaacaac       780
ggcgaagtct ataactcggc caagaagacc tgcagttgtc ctgatggcca atactggaac       840
ggcaagcaat gtgtttgccc gtacggccaa gtcttcaatg gcaagcagtg tgttcctgat       900
tgcggtaaag aagccacttt cgattacaac cagaagaagt gtgtttgcaa gaacaaggga       960
gagatctacg actccaagac caagacttgc agctgtcccg acggccaggt ttggaatggc      1020
aagcagtgcg tctgcccgta cggccaggtc ttcaacggca gcagtgtgt ccccgactgt       1080 ggcaaagacg ctacctatga ttacaatcag aagaagtgcg tttgcaagaa caagggagag      1140
gtctttgatc aaaagaccaa gacctgtagc tgccctgatg ccagtactg aatggaaag        1200 caatgtgcct gtccatacgg tcagatcttc aacggcaagc aatgtgtccc cgactgcgga      1260
aaagacgcca cctatgatta caatcagaag aagtgtgttt gcaagaacaa gggagaggtc      1320
tttgatcaaa agaccaagac ctgcagttgt cctgacggcc agtactggaa cggcaagcaa      1380
tgcgtctgtc catacggcaa gatctttgac ggaaagcaat gcgtagagga ctgcggcaag      1440
gatgctcatt tcgataacaa tcagaagaag tgcgtgtgca acaagaacgg agagatctac      1500
gactccaagt ccaagacctg tagctgcccc gacagccagt actgggacgg atccaagtgc      1560
gcatgcccct acggaaccgt ctgggacggc aagcactgca accaggattg cggcaaggac      1620
gctcatttcg acagcaacca gaagaagtgc gtgtgcaaca gcagggcga ggtttacgat       1680 agtaaatcca agacttgcag ctgccccgac ggccaatact gggacggttc caagtgtgcc      1740 tgccoctacg gcaaggtctg ggacggaaag caatgcgtgc caaactgcgg caaagatgct      1800
agctacgaca gcaagcagaa caagtgcgtg tgcaagaaca tcggccaagt ctttgatacg      1860
aagtccttga cttgcagctg cccagccgga acctcttgga atggccacgc ttgtgtgcag      1920
gattgtggca aggacgctca ttacgacagc aaccagaagt gctgcgtgtg caacaacaag      1980
ggcgagtctt atgatagtaa gtccaagact tgcagctgcc aggaaaacca gtattgggac      2040
ggcaacaagt gcgcgtgccc atacggatcg acttgggata gcagcaagaa gacttgtaag      2100
atgaactatc cttga                                                      2115
```

```
<210> SEQ ID NO 13
<211> LENGTH: 258
<212> TYPE: DNA
<213> ORGANISM: Fusarium oxysporum

<400> SEQUENCE: 13
```

```
atgcttctca acaaggcttt cctcggcgct cttctcgcca tgggcacagt caccgccctc        60
cccaaccccg acgctgagcc cgctgatctc gaggaacgca gcatccttca ccactgcggc       120
aagcacgctt cttgggatca cgccaagagc gagtgcgtgt ccacgactc cggcaaggtc        180 tacaccaaga agcaccacaa gtgcaagtgc cccaagggcg agaagtggca ccacattgag       240
aagaagtgca agaagtga                                                    258
```

```
<210> SEQ ID NO 14
<211> LENGTH: 258
<212> TYPE: PRT
<213> ORGANISM: Artificial Sequence
```

```
<220> FEATURE:
<223> OTHER INFORMATION: Deduced amino acid sequence encoded by SEQ ID
      NO:13; predicted full-length LB-12265 polypeptide
<220> FEATURE:
<221> NAME/KEY: SIGNAL
<222> LOCATION: (1)...(20)
<223> OTHER INFORMATION: Predicted signal peptide
<220> FEATURE:
<221> NAME/KEY: PROPEP
<222> LOCATION: (21)...(33)
<223> OTHER INFORMATION: Predicted propeptide region
<220> FEATURE:
<221> NAME/KEY: PEPTIDE
<222> LOCATION: (34)...(85)
<223> OTHER INFORMATION: Predicted mature peptide

<400> SEQUENCE: 14

Ala Thr Gly Cys Thr Thr Cys Thr Cys Ala Ala Cys Ala Ala Gly Gly
 1               5                   10                  15

Cys Thr Thr Thr Cys Cys Thr Cys Gly Gly Cys Gly Cys Thr Cys Thr
             20                  25                  30

Thr Cys Thr Cys Gly Cys Cys Ala Thr Gly Gly Cys Ala Cys Ala
         35                  40                  45

Gly Thr Cys Ala Cys Cys Gly Cys Cys Thr Cys Cys Cys Ala
50                   55                  60

Ala Cys Cys Cys Gly Ala Cys Gly Cys Thr Gly Ala Gly Cys Cys
65                  70                  75                  80

Cys Gly Cys Thr Gly Ala Thr Cys Thr Cys Gly Ala Gly Ala Ala
                85                  90                  95

Cys Gly Cys Ala Gly Cys Ala Thr Cys Cys Thr Thr Cys Ala Cys Cys
            100                 105                 110

Ala Cys Thr Gly Cys Gly Gly Cys Ala Ala Gly Cys Ala Cys Gly Cys
            115                 120                 125

Thr Thr Cys Thr Thr Gly Gly Gly Ala Thr Cys Ala Cys Gly Cys Cys
            130                 135                 140

Ala Ala Gly Ala Gly Cys Gly Ala Gly Thr Gly Cys Gly Thr Gly Thr
145                 150                 155                 160

Gly Cys Cys Ala Cys Gly Ala Cys Thr Cys Cys Gly Cys Ala Ala
                165                 170                 175

Gly Gly Thr Cys Thr Ala Cys Ala Cys Cys Ala Ala Gly Ala Ala Gly
            180                 185                 190

Cys Ala Cys Cys Ala Cys Ala Ala Gly Thr Gly Cys Ala Ala Gly Thr
            195                 200                 205

Gly Cys Cys Cys Ala Ala Gly Gly Cys Gly Ala Gly Ala
            210                 215                 220

Gly Thr Gly Gly Cys Ala Cys Cys Ala Cys Ala Thr Thr Gly Ala Gly
225                 230                 235                 240

Ala Ala Gly Ala Ala Gly Thr Gly Cys Ala Ala Gly Ala Ala Gly Thr
                245                 250                 255

Gly Ala

<210> SEQ ID NO 15
<211> LENGTH: 72
<212> TYPE: DNA
<213> ORGANISM: Artificial Sequence
<220> FEATURE:
<223> OTHER INFORMATION: Nucleotide sequence encoding the barley alpha
      amylase signal peptide
```

<400> SEQUENCE: 15
atggccaaca agcacctgtc cctctccctc ttcctcgtgc tcctcggcct ctccgcctcc    60
ctcgcctccg ga    72

<210> SEQ ID NO 16
<211> LENGTH: 24
<212> TYPE: PRT
<213> ORGANISM: Artificial Sequence
<220> FEATURE:
<223> OTHER INFORMATION: Barley alpha amylase signal peptide

<400> SEQUENCE: 16

Met Ala Asn Lys His Leu Ser Leu Ser Leu Phe Leu Val Leu Leu Gly
1               5                   10                  15

Leu Ser Ala Ser Leu Ala Ser Gly
            20

<210> SEQ ID NO 17
<211> LENGTH: 231
<212> TYPE: DNA
<213> ORGANISM: Artificial Sequence
<220> FEATURE:
<223> OTHER INFORMATION: Nucleotide sequence encoding the barley alpha
    amylase signal peptide linked to the nucleotide
    sequence encoding the mature LB-12265 peptide (SEQ
    ID NO:1)

<400> SEQUENCE: 17
atggccaaca agcacctgtc cctctccctc ttcctcgtgc tcctcggcct ctccgcctcc    60
ctcgcctccg gaagcatcct tcaccactgc ggcaagcacg cttcttggga tcacgccaag   120
agcgagtgcg tgtgccacga ctccggcaag gtctacacca agaagcacca caagtgcaag   180
tgccccaagg gcgagaagtg gcaccacatt gagaagaagt gcaagaagtg a            231

<210> SEQ ID NO 18
<211> LENGTH: 76
<212> TYPE: PRT
<213> ORGANISM: Artificial Sequence
<220> FEATURE:
<223> OTHER INFORMATION: Amino acid sequence encoded by SEQ ID NO:17;
    barley alpha amylase peptide joined to the mature
    LB-12265 peptide (SEQ ID NO:1)

<400> SEQUENCE: 18

Met Ala Asn Lys His Leu Ser Leu Ser Leu Phe Leu Val Leu Leu Gly
1               5                   10                  15

Leu Ser Ala Ser Leu Ala Ser Gly Ser Ile Leu His His Cys Gly Lys
            20                  25                  30

His Ala Ser Trp Asp His Ala Lys Ser Glu Cys Val Cys His Asp Ser
        35                  40                  45

Gly Lys Val Tyr Thr Lys Lys His His Lys Cys Lys Cys Pro Lys Gly
    50                  55                  60

Glu Lys Trp His His Ile Glu Lys Lys Cys Lys Lys
65                  70                  75

<210> SEQ ID NO 19
<211> LENGTH: 4
<212> TYPE: PRT
<213> ORGANISM: Artificial Sequence
<220> FEATURE:
<223> OTHER INFORMATION: Endoplasmic reticulum retention sequence

```
<400> SEQUENCE: 19

Lys Asp Glu Leu
 1

<210> SEQ ID NO 20
<211> LENGTH: 6
<212> TYPE: PRT
<213> ORGANISM: Artificial Sequence
<220> FEATURE:
<223> OTHER INFORMATION: Endoplasmic reticulum retention sequence

<400> SEQUENCE: 20

Ser Glu Lys Asp Glu Leu
 1               5

<210> SEQ ID NO 21
<211> LENGTH: 4
<212> TYPE: PRT
<213> ORGANISM: Artificial Sequence
<220> FEATURE:
<223> OTHER INFORMATION: Endoplasmic reticulum retention sequence

<400> SEQUENCE: 21

His Asp Glu Leu
 1

<210> SEQ ID NO 22
<211> LENGTH: 4
<212> TYPE: PRT
<213> ORGANISM: Artificial Sequence
<220> FEATURE:
<223> OTHER INFORMATION: Endoplasmic reticulum retention sequence

<400> SEQUENCE: 22

His Asp Glu Phe
 1

<210> SEQ ID NO 23
<211> LENGTH: 258
<212> TYPE: DNA
<213> ORGANISM: Unknown
<220> FEATURE:
<223> OTHER INFORMATION: Genomic sequence encoding full-length
      cr1n.pk0189.g4 polypeptide isolated from a fungal
      contaminant of Zea mays

<400> SEQUENCE: 23
atgcttctca caaggctttt cctcggcgcc ctcctcgcca tgggcacagt caccgccctc      60
cccaaccccg acgctgagcc cgttgatctc gaggatcgca gcatccttca ccactgtggc     120
aagcacgctt cctgggatca cgccaagagc gagtgcgtat gccacgactc cggcaaggtc     180
tacaccaaga agcaccacaa gtgcaagtgc cccaagggcg agaagtggca ccacattgag     240
aagaagtgca agaagtga                                                   258

<210> SEQ ID NO 24
<211> LENGTH: 85
<212> TYPE: PRT
<213> ORGANISM: Artificial Sequence
<220> FEATURE:
<223> OTHER INFORMATION: Deduced amino acid sequence encoded by SEQ ID
      NO:23; predicted sequence for full-length
      cr1n.pk0189.g4 polypeptide isolated from a fungal
      contaminant of Zea mays
```

```
<220> FEATURE:
<221> NAME/KEY: SIGNAL
<222> LOCATION: (1)...(20)
<223> OTHER INFORMATION: Predicted signal peptide
<220> FEATURE:
<221> NAME/KEY: PROPEP
<222> LOCATION: (21)...(33)
<223> OTHER INFORMATION: Predicted propeptide region
<220> FEATURE:
<221> NAME/KEY: PEPTIDE
<222> LOCATION: (34)...(85)
<223> OTHER INFORMATION: Predicted mature peptide

<400> SEQUENCE: 24

Met Leu Leu Asn Lys Ala Phe Leu Gly Ala Leu Leu Ala Met Gly Thr
1               5                   10                  15

Val Thr Ala Leu Pro Asn Pro Asp Ala Glu Pro Val Asp Leu Glu Asp
            20                  25                  30

Arg Ser Ile Leu His His Cys Gly Lys His Ala Ser Trp Asp His Ala
        35                  40                  45

Lys Ser Glu Cys Val Cys His Asp Ser Gly Lys Val Tyr Thr Lys Lys
    50                  55                  60

His His Lys Cys Lys Cys Pro Lys Gly Glu Lys Trp His His Ile Glu
65                  70                  75                  80

Lys Lys Cys Lys Lys
                85

<210> SEQ ID NO 25
<211> LENGTH: 19
<212> TYPE: PRT
<213> ORGANISM: Artificial Sequence
<220> FEATURE:
<223> OTHER INFORMATION: N-terminal fragment of LB-12265 polypeptide
      (SEQ ID NO:1)

<400> SEQUENCE: 25

Ser Ile Leu His His Cys Gly Lys His Ala Ser Trp Asp His Ala Lys
1               5                   10                  15

Ser Glu Cys

<210> SEQ ID NO 26
<211> LENGTH: 18
<212> TYPE: PRT
<213> ORGANISM: Artificial Sequence
<220> FEATURE:
<223> OTHER INFORMATION: N-terminal fragment of LB-12265 polypeptide
      (SEQ ID NO:1) from GluC digestion

<400> SEQUENCE: 26

Ser Ile Leu His His Cys Gly Lys His Ala Ser Trp Asp His Ala Lys
1               5                   10                  15

Ser Glu

<210> SEQ ID NO 27
<211> LENGTH: 18
<212> TYPE: PRT
<213> ORGANISM: Artificial Sequence
<220> FEATURE:
<223> OTHER INFORMATION: N-terminal fragment of LB-12265 polypeptide
      (SEQ ID NO:1) from GluC digestion
```

```
<400> SEQUENCE: 27

Ser Gly Lys Val Tyr Thr Lys Lys His His Cys Lys Cys Pro Lys
1               5                   10                  15

Gly Glu

<210> SEQ ID NO 28
<211> LENGTH: 6
<212> TYPE: PRT
<213> ORGANISM: Artificial Sequence
<220> FEATURE:
<223> OTHER INFORMATION: N-terminal fragment of LB-12265 polypeptide
      (SEQ ID NO:1) from GluC digestion

<400> SEQUENCE: 28

Lys Trp His His Ile Glu
1               5

<210> SEQ ID NO 29
<211> LENGTH: 7
<212> TYPE: PRT
<213> ORGANISM: Artificial Sequence
<220> FEATURE:
<223> OTHER INFORMATION: N-terminal fragment of LB-12265 polypeptide
      (SEQ ID NO:1) from GluC digestion

<400> SEQUENCE: 29

Ser Ile Leu His His Cys Gly
1               5

<210> SEQ ID NO 30
<211> LENGTH: 7
<212> TYPE: PRT
<213> ORGANISM: Artificial Sequence
<220> FEATURE:
<223> OTHER INFORMATION: N-terminal fragment of LB-12265 polypeptide
      (SEQ ID NO:1) from GluC digestion

<400> SEQUENCE: 30

Ser Gly Lys Val Tyr Thr Lys
1               5

<210> SEQ ID NO 31
<211> LENGTH: 5
<212> TYPE: PRT
<213> ORGANISM: Artificial Sequence
<220> FEATURE:
<223> OTHER INFORMATION: N-terminal fragment of LB-12265 polypeptide
      (SEQ ID NO:1) from GluC digestion

<400> SEQUENCE: 31

Lys Lys Cys Lys Lys
1               5

<210> SEQ ID NO 32
<211> LENGTH: 46
<212> TYPE: DNA
<213> ORGANISM: Artificial Sequence
<220> FEATURE:
<223> OTHER INFORMATION: PCR sense primer 93229

<400> SEQUENCE: 32
ccatcaggat ccggcggcca tgcttctcaa caaggctttc ctcggc           46
```

<210> SEQ ID NO 33
<211> LENGTH: 49
<212> TYPE: DNA
<213> ORGANISM: Artificial Sequence
<220> FEATURE:
<223> OTHER INFORMATION: PCR antisense primer 93231

<400> SEQUENCE: 33
cgttgtgata tctcacttct tgcacttctt ctcaatgtgg tgccacttc    49

<210> SEQ ID NO 34
<211> LENGTH: 248
<212> TYPE: PRT
<213> ORGANISM: Gibberella zeae

<400> SEQUENCE: 34

Met Arg Phe Ser Asn Leu Phe Leu Gly Ala Val Phe Ala Val Thr Ser
 1               5                  10                  15

Val Ala Ala Met Ala Asn Pro Ala Ala Glu Ala Gly Ser Leu Met Glu
            20                  25                  30

Arg Ser Lys His His His Asp Cys Gly Lys His Ala Ser Tyr Asn Thr
        35                  40                  45

Glu Lys Lys Glu Cys Val Cys His Val Ser Gly Glu Thr Tyr His Lys
    50                  55                  60

Lys His His Lys Cys Lys Lys Pro Lys Glu Asp Lys Lys His His Ser
65                  70                  75                  80

Arg Asp Val Leu Glu Glu Arg Ser Pro Lys Lys Asp Glu His Glu His
                85                  90                  95

Cys Gly Lys His Ala Ser Phe Asn Glu Glu Lys Lys Glu Cys Val Cys
            100                 105                 110

His Asp Lys Ser Glu Val Phe Glu Lys His His Lys Lys Cys Lys Lys
        115                 120                 125

Ala Lys Asp Glu Lys Lys Lys Asp Asp Lys Lys His His Ser Arg Asp
    130                 135                 140

Val Leu Glu Glu Arg Asp Pro Lys Lys Asp Lys His His Asp His Cys
145                 150                 155                 160

Gly Lys His Ala Ser Tyr Ser Glu Glu Lys Lys Glu Cys Val Cys His
                165                 170                 175

Asn Lys Ala Glu Val Phe Glu Arg Lys His Lys Lys Cys Lys Lys His
            180                 185                 190

Ile Ser Leu Arg Ser Ile Phe Asn His Cys Gly Arg His Ala Tyr Tyr
        195                 200                 205

Asp Glu Ala Lys Lys Glu Cys Ile Cys His Asp Ala Gly Lys Asp Phe
    210                 215                 220

Leu Lys Lys His Lys Thr Cys Ala Cys Pro Gln Gly Glu Lys Trp His
225                 230                 235                 240

His Ile Glu Arg Lys Cys Lys Ala
                245

<210> SEQ ID NO 35
<211> LENGTH: 53
<212> TYPE: PRT
<213> ORGANISM: Artificial Sequence
<220> FEATURE:
<223> OTHER INFORMATION: Domain B of SEQ ID NO:34

-continued

```
<400> SEQUENCE: 35

Ser Pro Lys Lys Asp Glu His Glu His Cys Gly Lys His Ala Ser Phe
 1               5                  10                  15

Asn Glu Glu Lys Lys Glu Cys Val Cys His Asp Lys Ser Glu Val Phe
                20                  25                  30

Glu Lys His His Lys Lys Cys Lys Lys Ala Lys Asp Glu Lys Lys Lys
            35                  40                  45

Asp Asp Lys Lys His
        50

<210> SEQ ID NO 36
<211> LENGTH: 45
<212> TYPE: PRT
<213> ORGANISM: Artificial Sequence
<220> FEATURE:
<223> OTHER INFORMATION: Domain C of SEQ ID NO:34

<400> SEQUENCE: 36

Lys Lys Asp Lys His His Asp His Cys Gly Lys His Ala Ser Tyr Ser
 1               5                  10                  15

Glu Glu Lys Lys Glu Cys Val Cys His Asn Lys Ala Glu Val Phe Glu
                20                  25                  30

Arg Lys His Lys Lys Cys Lys Lys His Ile Ser Leu Arg
            35                  40                  45

<210> SEQ ID NO 37
<211> LENGTH: 52
<212> TYPE: PRT
<213> ORGANISM: Artificial Sequence
<220> FEATURE:
<223> OTHER INFORMATION: Domain D of SEQ ID NO:34

<400> SEQUENCE: 37

Ser Ile Phe Asn His Cys Gly Arg His Ala Tyr Tyr Asp Glu Ala Lys
 1               5                  10                  15

Lys Glu Cys Ile Cys His Asp Ala Gly Lys Asp Phe Leu Lys Lys His
                20                  25                  30

Lys Thr Cys Ala Cys Pro Gln Gly Glu Lys Trp His His Ile Glu Arg
            35                  40                  45

Lys Cys Lys Ala
        50
```